US011046661B2

(12) United States Patent
Chang et al.

(10) Patent No.: US 11,046,661 B2
(45) Date of Patent: Jun. 29, 2021

(54) METHOD FOR PRODUCING LACTAM COMPOUND, AND LACTAM COMPOUND PRODUCED THEREBY

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Sukbok Chang, Daejeon (KR); Seung Youn Hong, Daejeon (KR); Yoon Su Park, Daejeon (KR); Yeongyu Hwang, Daejeon (KR); Yeong Bum Kim, Daejeon (KR)

(73) Assignees: INSTITUTE FOR BASIC SCIENCE, Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/959,863

(22) PCT Filed: Jan. 2, 2019

(86) PCT No.: PCT/KR2019/000056
§ 371 (c)(1),
(2) Date: Jul. 2, 2020

(87) PCT Pub. No.: WO2019/135604
PCT Pub. Date: Jul. 11, 2019

(65) Prior Publication Data
US 2020/0331871 A1    Oct. 22, 2020

(30) Foreign Application Priority Data

Jan. 2, 2018  (KR) .................. 10-2018-0000421
Dec. 28, 2018  (KR) .................. 10-2018-0173117

(51) Int. Cl.
*C07D 273/01* (2006.01)
*C07D 413/06* (2006.01)
*C07D 209/34* (2006.01)
*C07D 491/22* (2006.01)
*C07D 209/54* (2006.01)
*C07D 205/12* (2006.01)
*C07D 215/227* (2006.01)

(52) U.S. Cl.
CPC ......... *C07D 273/01* (2013.01); *C07D 205/12* (2013.01); *C07D 209/34* (2013.01); *C07D 209/54* (2013.01); *C07D 215/227* (2013.01); *C07D 413/06* (2013.01); *C07D 491/22* (2013.01)

(58) Field of Classification Search
CPC .................................................. C07D 273/01
See application file for complete search history.

(56) References Cited

U.S. PATENT DOCUMENTS

2013/0117518 A1    5/2013  Kobayashi

FOREIGN PATENT DOCUMENTS

| JP | 58-192874 A | 11/1983 | |
| JP | 58192874 | * 11/1983 | ........... C07D 261/20 |
| WO | WO 2012/001780 A1 | 1/2012 | |

OTHER PUBLICATIONS

Jain et al., Oxidative amidation in the napthalene series. Synlett (2015). vol. 26, No. 5, pp. 631-634.*
International Search Report dated Apr. 3, 2019, in connection with corresponding International Patent Application No. PCT/KR2019/000056.
Jain, N. et al., "Oxidative Amidation in the Naphthalene Series," Synlett. 2015, vol. 26, No. 05, pp. 631-634, cited in NPL No. 1.
Chemical Abstract compounds, STN express, Entered STN: Nov. 16, 1984, cited in NPL No. 1.
Zhong, Z. et al., "Synthesis and Catalytic Activity of Amino Acids and Metallopeptides with Catalytically Active Metallocyclic Side Chains," Organometallies. 2012, vol. 31, No. 21, pp. 7328-7331, cited in NPL No. 1.
Hwang, Y. et al., "Revisiting Arene C(sp2)-H Amidation by Intramolecular Transfer of Iridium Nitrenoids: Evidence for a Spirocyclization Pathway," Angewandte Chemie, Aug. 27, 2018, vol. 130, No. 41, pp. 13753-13757, cited in NPL No. 1.
Hong, S. Y. et al., Selective formation of gamma-lactams via C-H amidation enabled by tailored iridium catalysts,, Science. Mar. 2, 2018, vol. 359, No. 6379, pp. 1013-1021, cited in NPL No. 1.
Hong, S. Y. et al., "Ir(III)-Catalyzed Stereoselective Haloamidation of Alkynes Enabled by Ligand Participation," Journal of the American Chemical Society, Sep. 14, 2018, vol. 140, No. 39, pp. 12359-12363, cited in NPL No. 1.
Notice of Allowance issued for corresponding Korean Patent Application No. 10-2018-0173117 dated Nov. 5, 2020, along with an English translation.

* cited by examiner

*Primary Examiner* — Paul V Ward
(74) *Attorney, Agent, or Firm* — Hauptman Ham, LLP

(57) ABSTRACT

The present invention relates to a method for producing a lactam compound from dioxazolone in the presence of a catalyst having a particular ligand, and to a lactam compound produced thereby, and can produce a lactam compound with excellent selectivity and an excellent yield by using the combination of a starting material having a particular functional group and a particular catalyst having a particular ligand.

14 Claims, No Drawings

METHOD FOR PRODUCING LACTAM COMPOUND, AND LACTAM COMPOUND PRODUCED THEREBY

CROSS-REFERENCE TO RELATED APPLICATION

The present application is a national stage filing under 35 U.S.C § 371 of PCT application number PCT/KR2019/000056 filed on Jan. 2, 2019 which is based upon and claims the benefit of priorities to Korean Patent Application No. 10-2018-0000421, filed on Jan. 2, 2018 and Korean Patent Application No. 10-2018-0173117, filed on Dec. 28, 2018, in the Korean Intellectual Property Office, which are incorporated herein in their entireties by reference.

TECHNICAL FIELD

The present invention relates to a method for producing a lactam compound and a lactam compound prepared therefrom, and more particularly, to a method of preparing a lactam compound using a specific catalyst and a lactam compound prepared therefrom.

BACKGROUND ART

The most preferred method of purifying hydrocarbon with low added value which is supplied in large quantities in petroleum or a renewable biomass source into a chemical material with high added value is a reaction of oxidizing a C—H bond using a catalyst.

Therefore, the reaction of oxidizing a C—H bond using a catalyst is regarded as being one of the most important reactions in chemistry, and a nitration reaction of an aliphatic compound having a C—H compound using a catalyst is a very important reaction which is most commonly used in various organic synthesis, medicines, and material chemistry.

An effective and general method for performing a C—N coupling reaction is to convert a nucleophilic amino functional group into an electrophilic nitrene having a much stronger reactivity in a C—H amidation reaction using a metal catalyst.

This reaction is very efficient and the related reactions have been studied by many researchers for a long time.

As an example, it is known by Breslow et al. that in the synthesis of oxathiazolidine catalyzed by Fe(III) or Rh(II), ROSO$_2$N=IR' (iminoiodinanes) which is a reactive peroxide may serve as a sulfonylnitrene precursor, and thereafter, various methods related thereto have been studied.

However, C—H amidation has an unsolved problem for being applied to preparation of cyclic amides such as lactam which is very useful for a raw material and an intermediate in organic synthesis and a medicinal use, and the route thereof is also unclear.

The simplest precursor and the most important intermediate which may directly produce a cyclic amide compound is known as carbonylnitrene produced in an in-situ reaction.

Therefore, in principle, it is considered that in a catalytic reaction using a metal, the reaction proceeds through a main metal-nitrene intermediate and then a C—H bond is inserted to produce an aziheterocyclic compound corresponding thereto.

However, the main reason for not synthesizing a lactam compound by the C—H amidation reaction is that a metal-carbonylnitrene intermediate which is regarded as an intermediate is unstable and easily produce isocyanate by Curtius type rearrangement.

This instability is also accounted for as acyl azide as a synthesis precursor under photolysis, pyrolysis, and transition metal catalyst conditions.

Accordingly, acyl azide is inappropriate as an amide source of a C—H amidation reaction and a specific amide source is needed, and furthermore, a study on a catalyst for preparing a lactam compound with excellent selectivity and yield is also needed.

DISCLOSURE

Technical Problem

While trying to solve the problem described above, the present inventor found that when a combination of a starting material having a specific functional group and a specific catalyst having a specific ligand is used, a lactam compound may be prepared with excellent selectivity and yield, thereby completing the present invention.

Another object of the present invention is to provide a lactam compound prepared according to the method of preparing a lactam compound of the present invention.

Technical Solution

The present invention is to provide a method of preparing a lactam compound with excellent selectivity and yield by a combination of a specific catalyst and a specific starting material, and in one general aspect, a method of preparing a lactam compound includes: amidating a 3-substituted dioxazol-one compound in the presence of a catalyst represented by the following Chemical Formula 1 and a base to prepare a lactam compound:

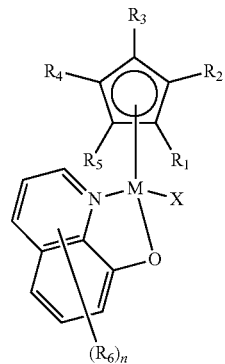

[Chemical Formula 1]

wherein
M is iridium, rhodium, ruthenium, or cobalt;
X is a halogen;
$R_1$ to $R_5$ are independently of one another hydrogen or (C1-C7)alkyl; and
$R_6$ is a halogen, (C1-C20)alkyl, halo(C1-C20)alkyl, (C1-C20)alkoxy, (C6-C20)aryl, or (C3-C20)heteroaryl;
n is an integer of 0 to 6.

Specifically, the method of preparing a lactam compound according to an embodiment of the present invention may include amidating a 3-substituted dioxazol-one compound of the following Chemical Formula 2 in the presence of the catalyst represented by Chemical Formula 1 and the base to prepare a lactam compound of the following Chemical Formula 3:

[Chemical Formula 2]

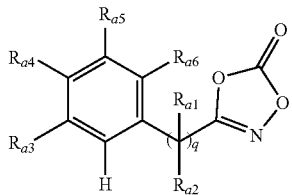

[Chemical Formula 3]

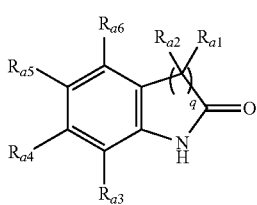

wherein $R_{a1}$ and $R_{a2}$ are independently of each other hydrogen, (C1-C20)alkyl, (C6-C20)aryl, or (C3-C20)heterocycloalkyl;

$R_{a3}$ to $R_{a6}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

Specifically, the method of preparing a lactam compound according to a second embodiment of the present invention may include amidating a 3-substituted dioxazol-one compound of the following Chemical Formula 4 in the presence of the catalyst represented by Chemical Formula 1 and the base to prepare a lactam compound of the following Chemical Formula 5:

[Chemical Formula 4]

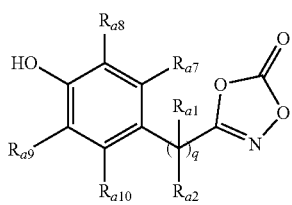

[Chemical Formula 5]

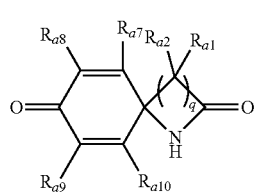

wherein $R_{a1}$ and $R_{a2}$ are independently of each other hydrogen, (C1-C20)alkyl, (C6-C20)aryl, or (C3-C20)heterocycloalkyl;

$R_{a7}$ to $R_{a10}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

Specifically, the method of preparing a lactam compound according to a third embodiment of the present invention may include amidating a 3-substituted dioxazol-one compound of the following Chemical Formula 6 in the presence of the catalyst represented by Chemical Formula 1 and the base to prepare a lactam compound of the following Chemical Formula 7:

[Chemical Formula 6]

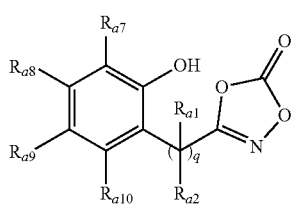

[Chemical Formula 7]

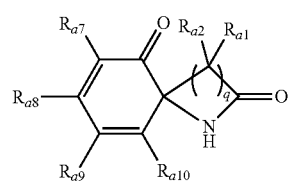

wherein $R_{a1}$ and $R_{a2}$ are independently of each other hydrogen, (C1-C20)alkyl, (C6-C20)aryl, or (C3-C20)heterocycloalkyl;

$R_{a7}$ to $R_{a10}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

Specifically, the method of preparing a lactam compound according to a fourth embodiment of the present invention may include amidating a 3-substituted dioxazol-one compound of the following Chemical Formula 8 in the presence of the catalyst represented by Chemical Formula 1 and the base to prepare a lactam compound of the following Chemical Formula 9:

[Chemical Formula 8]

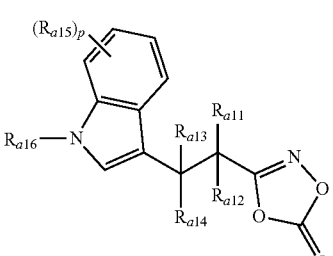

-continued

[Chemical Formula 9]

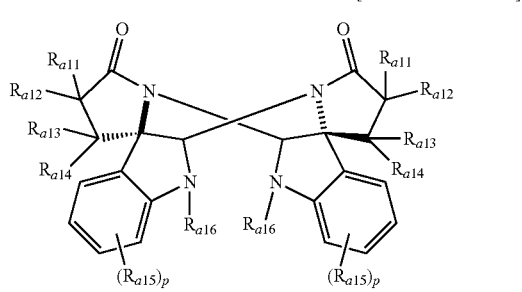

wherein $R_{a11}$ to $R_{a14}$ are independently of one another hydrogen or (C1-C20)alkyl;

$R_{a15}$ is a halogen, (C1-C20)alkyl, halo (C1-C20) alkyl, (C2-C20)alkenyl, (C2-C20)alkynyl, (C1-C20)alkoxy, (C6-C20)aryl, or (C3-C20)heteroaryl;

$R_{a16}$ is hydrogen or (C1-C7) alkyl; and p is an integer of 0 to 4.

Preferably, the catalyst according to an exemplary embodiment of the present invention may be used at 0.01 to 0.1 mol with respect to 1 mol of the 3-substituted dioxazol-one compound.

Preferably, the base according to an exemplary embodiment of the present invention may be one or two or more selected from NaBAr$^F$$_4$ (sodium tetrakis[3,5-bis(trifluoromethyl)phenyl]borate), AgSbF$_6$ (silver hexafluoroantimonate (V)), AgNTf$_2$ (silver bis(trifluoromethanesulfonyl)imide), AgBF$_4$ (silver tetrafluoroborate), AgPF$_6$ (silver hexafluorophosphate), AgOTf (silver trifluoromethanesulfonate), and AgOAc (Silver acetate), and may be used at 0.01 to 0.1 mol with respect to 1 mol of the 3-substituted dioxazol-one compound.

Preferably, the amidation according to an exemplary embodiment of the present invention may be performed at 20 to 80° C.

In terms of having more improved selectivity and yield, preferably, in Chemical Formula 1 according to an exemplary embodiment of the present invention, M may be iridium; X may be chloro; $R_1$ to $R_5$ may be independently of one another (C1-C20)alkyl; $R_6$ may be a halogen; and n may be an integer of 0 to 2.

Preferably, in Chemical Formulae 2 and 3 according to an exemplary embodiment of the method of preparing a lactam compound of the present invention, $R_{a1}$ and $R_{a2}$ may be independently of each other hydrogen, (C6-C20)aryl, or phthalimido; $R_{a3}$ to $R_{a6}$ may be independently of one another hydrogen, a halogen, (C1-C20)alkyl, halo(C1-C20)alkyl, or (C1-C20)alkoxy, or may be connected to an adjacent substituent to form an aromatic ring with or without a fused ring; and q may be an integer of 1 or 2.

Preferably, in Chemical Formulae 4 to 7 according to an exemplary embodiment of the method of preparing a lactam compound of the present invention, $R_{a1}$ and $R_{a2}$ may be independently of each other hydrogen or phthalimido; $R_{a7}$ to $R_{a10}$ may be independently of one another hydrogen, a halogen, (C1-C20)alkyl, or (C1-C20)alkoxy, or may be connected to an adjacent substituent to form an aromatic ring with or without a fused ring; and q may be an integer of 1 or 2.

Preferably, in Chemical Formulae 8 and 9 according to an exemplary embodiment of the method of preparing a lactam compound of the present invention, $R_{a11}$ to $R_{a14}$ may be independently of one another hydrogen; $R_{15}$ may be a halogen, (C1-C20)alkyl, or (C1-C20)alkoxy; $R_{a16}$ may be hydrogen or (C1-C20)alkyl; and q may be an integer of 0 or 1.

In another general aspect, a lactam compound represented by Chemical formula 3, Chemical Formula 5, Chemical Formula 7, or Chemical Formula 9, prepared according to the method of preparing a lactam compound of the present invention is provided.

Advantageous Effects

The method of preparing a lactam compound of the present invention uses a starting material having a specific functional group in the presence of a specific catalyst having a specific ligand, thereby easily preparing a high-purity lactam compound with high selectivity and yield, and thus, the lactam compound prepared therefrom is useful as a raw material, an intermediate, and the like in various fields.

[Best Mode]

Hereinafter, the method of preparing a lactam compound from a dioxazol-one compound in the presence of a specific catalyst will be described in detail, but the present invention is not limited thereto.

"Alkyl", "alkoxy", and a substituent containing "alkyl" described herein refer to a hydrocarbon radical in a linear or branched form having 1 to 20 carbon atoms.

"Alkenyl" described herein is an organic radical derived from a hydrocarbon containing one or more double bonds, and "Alkynyl" herein is an organic radical derived from a hydrocarbon containing one or more double bonds.

"Haloalkyl" described herein refers to one or more hydrogens of the alkyl being substituted by one or more halogens, preferably fluorines.

"Aryl" described herein is an organic radical derived from an aromatic hydrocarbon by removal of one hydrogen, including a monocyclic or fused ring system containing appropriately 4 to 7, preferably 5 or 6 ring atoms in each ring, and even including a form in which a plurality of aryls are connected by a single bond. A specific example includes phenyl, naphthyl, biphenyl, terphenyl, anthryl, indenyl, fluorenyl, phenanthryl, triphenylenyl, pyrenyl, perylenyl, crycenyl, naphthacenyl, fluoranthenyl, and the like. Naphthyl includes 1-naphthyl and 2-naphthyl, anthryl includes 1-anthryl, 2-anthryl, and 9-anthryl, and fluorenyl includes all of 1-fluorenyl, 2-fluorenyl, 3-fluorenyl, 4-fluorenyl, and 9-fluorenyl.

"Heteroaryl" described herein refers to an aryl group containing 1 to 4 heteroatoms selected from B, N, O, S, P(=O), Si, and P as an aromatic ring backbone atom, and carbons as remaining aromatic ring backbone atoms, and is a 5- or 6-membered monocyclic heteroaryl and a polycyclic heteroaryl fused with one or more benzene rings, which may be partially saturated. In addition, heteroaryl in the present invention also includes a form in which one or more heteroaryls are connected by a single bond.

"Heterocycloalkyl" described herein refers to a non-aromatic monocyclic or polycyclic ring system having 3 to 20 carbon atoms containing 1 to 4 heteroatoms selected from B, N, O, S, P(=O), Si, and P, and phthalimido

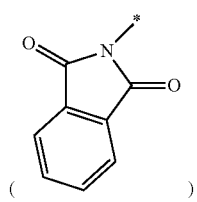

of the present invention is included therein.

A fused ring of "an aromatic ring or an alicyclic ring containing a fused ring" described herein may be an aromatic ring or an alicyclic ring, preferably an aromatic ring or alicyclic ring, and specifically a C6-C12 aromatic ring or a C1-C12 alicyclic ring, but is not limited thereto.

In addition, a "(C1-C20)alkyl" group described herein is preferably (C1-C10)alkyl, and more preferably (C1-C7) alkyl, a "(C6-C20)aryl" group is preferably (C6-C12)aryl, a "(C3-C30)heteroaryl" group is preferably (C3-C12)heteroaryl, and a "(C3-C20)heterocycloalkyl" group is preferably (C3-C12)heterocycloalkyl.

The present invention is to provide a method of preparing a lactam compound with excellent selectivity, and the method of preparing a lactam compound of the present invention includes: amidating a 3-substituted dioxazol-one compound in the presence of a catalyst represented by the following Chemical Formula 1 and a base to prepare a lactam compound:

[Chemical Formula 1]

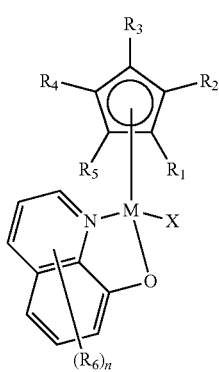

wherein

M is iridium, rhodium, ruthenium, or cobalt;

X is a halogen;

$R_1$ to $R_5$ are independently of one another hydrogen or (C1-C20)alkyl;

$R_6$ is a halogen, (C1-C20)alkyl, halo(C1-C20)alkyl, (C1-C20)alkoxy, (C6-C20)aryl, or (C3-C20)heteroaryl; and n is an integer of 0 to 6.

In the method of preparing a lactam compound of the present invention, the lactam compound may not be prepared with catalysts other than the catalyst represented by Chemical Formula 1, and the catalyst represented by Chemical Formula 1 may be used to obtain the lactam compound with high selectivity and yield under mild conditions.

Furthermore, the method of a lactam compound of the present invention may easily produce the lactam compound with high selectivity and yield by a combination of the catalyst represented by Chemical Formula 1 and a 3-substituted dioxazol-one compound as a specific starting material.

That is, in the method of preparing a lactam compound of the present invention, a 3-substituted dioxazol-one compound as a specific starting material is introduced instead of carbonylnitrenes which has been used as a conventional starting material, thereby easily producing a lactam compound unlike the unstable carbonylnitrenes, and furthermore, may produce a lactam compound with high selectivity under mild conditions.

Specifically, the method of preparing a lactam compound according to an embodiment of the present invention may include amidating a 3-substituted dioxazol-one compound of the following Chemical Formula 2 in the presence of the catalyst represented by Chemical Formula 1 and the base to prepare a lactam compound of the following Chemical Formula 3:

[Chemical Formula 2]

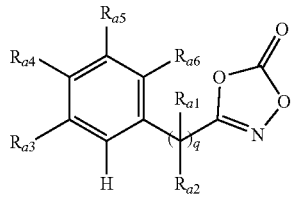

[Chemical Formula 3]

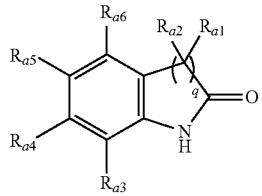

wherein $R_{a1}$ and $R_{a2}$ are independently of each other hydrogen, (C1-C20)alkyl, (C6-C20)aryl, or (C3-C20)heterocycloalkyl;

$R_{a3}$ to $R_{a6}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

Specifically, the method of preparing a lactam compound according to a second embodiment of the present invention may include amidating a 3-substituted dioxazol-one compound of the following Chemical Formula 4 in the presence of the catalyst represented by Chemical Formula 1 and the base to prepare a lactam compound of the following Chemical Formula 5:

[Chemical Formula 4]

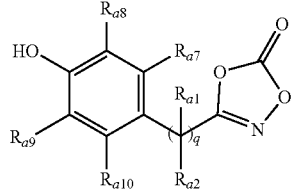

[Chemical Formula 5]

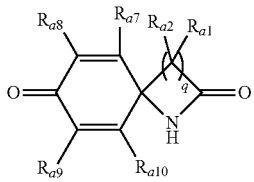

wherein $R_{a1}$ and $R_{a2}$ are independently of each other hydrogen, (C1-C20)alkyl, (C6-C20)aryl, or (C3-C20)heterocycloalkyl;

$R_{a7}$ to $R_{a10}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

Specifically, the method of preparing a lactam compound according to a third embodiment of the present invention may include amidating a 3-substituted dioxazol-one compound of the following Chemical Formula 6 in the presence of the catalyst represented by Chemical Formula 1 and the base to prepare a lactam compound of the following Chemical Formula 7:

[Chemical Formula 6]

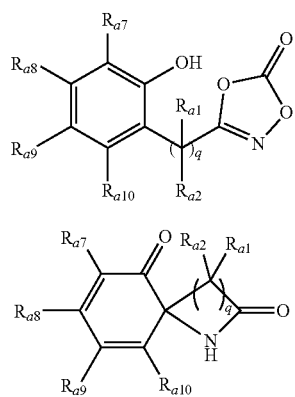

[Chemical Formula 7]

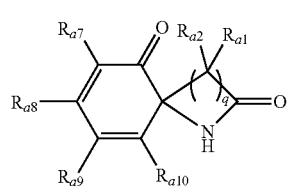

wherein $R_{a1}$ and $R_{a2}$ are independently of each other hydrogen, (C1-C20)alkyl, (C6-C20)aryl, or (C3-C20)heterocycloalkyl;

$R_{a7}$ to $R_{a10}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

Specifically, the method of preparing a lactam compound according to a fourth embodiment of the present invention may include amidating a 3-substituted dioxazol-one compound of the following Chemical Formula 8 in the presence of the catalyst represented by Chemical Formula 1 and the base to prepare a lactam compound of the following Chemical Formula 9:

[Chemical Formula 8]

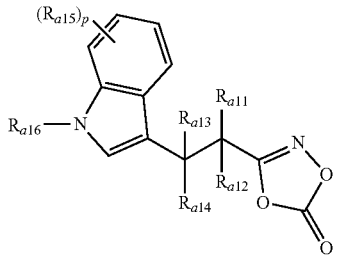

[Chemical Formula 9]

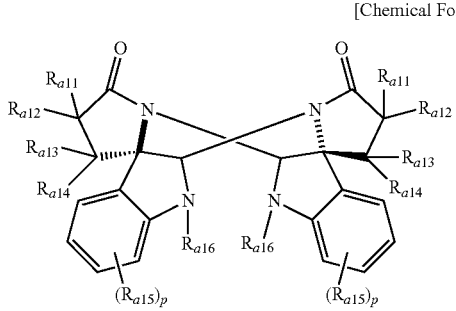

wherein $R_{a11}$ to $R_{a14}$ are independently of one another hydrogen or (C1-C20)alkyl;

$R_{a15}$ is a halogen, (C1-C20) alkyl, halo (C1-C20) alkyl, (C2-C20)alkenyl, (C2-C20)alkynyl, (C1-C20)alkoxy, (C6-C20)aryl, or (C3-C20)heteroaryl;

$R_{a16}$ is hydrogen or (C1-C7)alkyl; and p is an integer of 0 to 4.

Preferably, the base according to an exemplary embodiment of the method of preparing a lactam compound of the present invention may be one or two or more selected from NaBAr$^F_4$ (sodium tetrakis[3,5-bis(trifluoromethyl)phenyl]borate), AgSbF$_6$ (silver hexafluoroantimonate(V)), AgNTf$_2$ (silver bis(trifluoromethanesulfonyl)imide), AgBF$_4$ (silver tetrafluoroborate), AgPF$_6$ (silver hexafluorophosphate), AgOTf (silver trifluoromethanesulfonate), and AgOAc (silver acetate), preferably one or two or more selected from NaBAr$^F_4$ (tetrakis[3,5-bis(trifluoromethyl)phenyl]borate), AgSbF$_6$, AgNTf$_2$, and AgBF$_4$, and may be used at 0.01 to 0.1 mol, preferably 0.01 to 0.07 mol with respect to 1 mol of the 3-substituted dioxazol-one compound.

The catalyst of Chemical Formula 1 according to an exemplary embodiment of the present invention may be used at 0.01 to 0.1 mol, preferably 0.03 to 0.07 mol with respect to 1 mol of the 3-substituted dioxazol-one compound.

Preferably, amidation according to an exemplary embodiment of the present invention may be performed by stirring at 20 to 80° C., preferably 40 to 80° C. for 8 to 24 hours, preferably 8 to 18 hours.

In the method of preparing a lactam compound according to an exemplary embodiment of the present invention, amidation may be performed under an organic solvent, and it is not necessary to limit the organic solvent as long as it dissolves the reaction material. As the organic solvent according to an exemplary embodiment of the present invention, one or more selected from 1,1,1,3,3,3-hexafluoro-2-propanol, dichloromethane, dichloroethane, nitromethane, toluene, and benzene may be used, and considering a solubility of the reactant and ease of removal, dichloromethane, dichloroethane, and 1,1,1,3,3,3-hexafluoro-2-propanol may be used as a solvent.

In terms of preparing the lactam compound with high selectivity and yield, preferably, in Chemical Formula 1 according to an exemplary embodiment of the method of preparing a lactam compound of the present invention, M may be iridium; X may be chloro; $R_1$ to $R_5$ may be independently of one another (C1-C20)alkyl; $R_6$ may be a halogen; and n may be an integer of 0 to 2, in Chemical Formulae 2 and 3 according to an exemplary embodiment, $R_{a1}$ and $R_{a2}$ may be independently of each other hydrogen, (C6-C20)aryl, or phthalimido; $R_{a3}$ to $R_{a6}$ may be independently of one another hydrogen, a halogen, (C1-C20)alkyl, halo(C1-C20)alkyl, or (C1-C20)alkoxy, or may be connected to an adjacent substituent to form an aromatic ring with or without a fused ring; and q may be an integer of 1 or 2, in Chemical Formulae 4 to 7 according to an exemplary embodiment, $R_{a1}$ and $R_{a2}$ may be independently of each other hydrogen or phthalimido; $R_{a7}$ to $R_{a10}$ may be independently of one another hydrogen, a halogen, (C1-C20) alkyl, or (C1-C20)alkoxy, or may be connected to an adjacent substituent to form an aromatic ring with or without a fused ring; and q may be an integer of 1 or 2, and in Chemical Formulae 8 and 9 according to an exemplary embodiment, $R_{a11}$ to $R_{a14}$ may be independently of one another hydrogen; $R_{a15}$ may be a halogen, (C1-C20)alkyl, or (C1-C20)alkoxy; $R_{a16}$ may be hydrogen or (C1-C20)alkyl; and q may be an integer of 0 or 1.

In addition, the present invention provides a lactam compound represented by the following Chemical formula 3, Chemical Formula 5, Chemical Formula 7, or Chemical Formula 9:

[Chemical Formula 3]

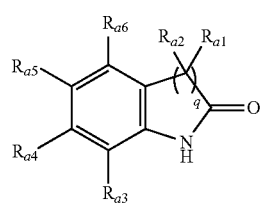

[Chemical Formula 5]

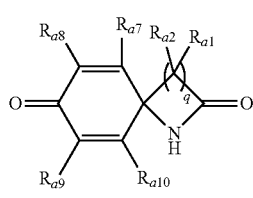

[Chemical Formula 7]

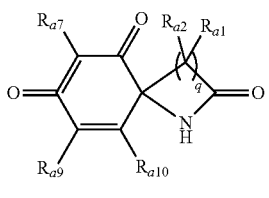

[Chemical Formula 9]

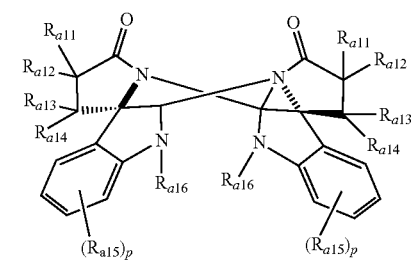

wherein $R_{a1}$ and $R_{a2}$ are independently of each other hydrogen, (C1-C20)alkyl, (C6-C20)aryl, or (C3-C20)heterocycloalkyl;

$R_{a3}$ to $R_{a6}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring;

$R_{a7}$ to $R_{a10}$ are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring;

$R_{a11}$ to $R_{a14}$ are independently of one another hydrogen or (C1-C20)alkyl;

$R_{a15}$ is a halogen, (C1-C20) alkyl, halo (C1-C20) alkyl, (C2-C20)alkenyl, (C2-C20)alkynyl, (C1-C20)alkoxy, (C6-C20)aryl, or (C3-C20)heteroaryl;

$R_{a16}$ is hydrogen or (C1-C20)alkyl;

p is an integer of 0 to 4; and q is an integer of 1 or 2.

Hereinafter, the constitution of the present invention will be described in detail by the Examples, and the following Examples are for better understanding of the present invention, but the scope of the present invention is not limited thereto.

EXAMPLE 1: PREPARATION OF CATALYST

[Examples 1] Preparation of Catalyst A

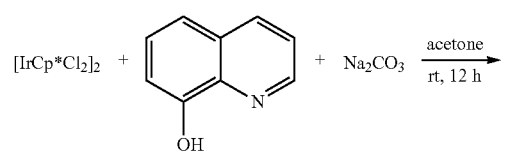

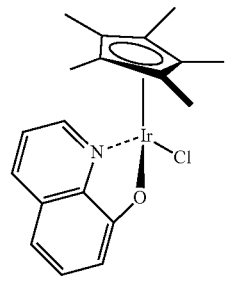

A

[IrCp*Cl$_2$]$_2$ (Cp*: pentamethylcyclopentadienyl) (0.20 g, 0.25 mmol), quinolin-8-ol (72.6 mg, 0.50 mmol), sodium carbonate (0.21 g, 2.0 mmol), and acetone (10 mL) were added to a vial and the mixture was stirred at room temperature for 12 hours. After the reaction was completed, the reactants were filtered with celite (dichloromethane (15 mL×3)), the solvent was removed by distillation under reduced pressure, and separation and purification were performed by column chromatography (n-hexane/acetone=2:1 to 1:1) to prepare Catalyst A.

8-Hydroxyquinoline Bound Cp*-Iridium Complex (Catalyst A)

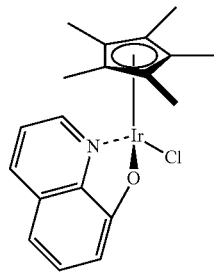

Orange solid (0.20 g, 80%); $^1$H NMR (600 Hz, CDCl$_3$) δ 8.54 (d, J=4.9 Hz, 1H), 8.03 (d, J=8.3 Hz, 1H), 7.36 (t, J=7.9 Hz, 1H), 7.30 (dd, J=8.3, 4.9 Hz, 1H), 7.00 (d, J=7.9 Hz, 1H), 6.78 (d, J=7.9 Hz, 1H), 1.73 (s, 15H); $^{13}$C NMR (150 MHz, CDCl$_3$) δ 169.1, 146.0, 145.8, 137.7, 131.0, 130.7, 121.9, 115.6, 110.9, 84.8 (Cp*), 8.9 (Cp*); IR (cm$^{-1}$) 1564, 1455, 1367, 1320, 1111, 826, 751, 512; HRMS (EI) m/z calcd. for C$_{19}$H$_{21}$ClIrNO [M]$^+$: 507.0941. found: 507.0943.

[Examples 2] Preparation of Catalyst B

Catalyst B was prepared in the same manner as in Example 1, except that 5,7-dichloroquinolin-8-ol (0.50 mmol) was used instead of quinolin-8-ol.

5,7-Dichloroquinolin-8-ol Bound Cp*-Iridium Complex (Catalyst B)

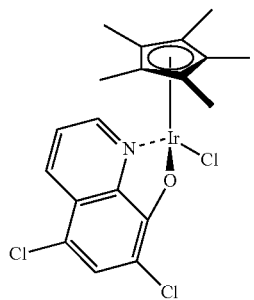

Yellow solid (0.19 g, 67%); $^1$H NMR (800 MHz, CD$_2$Cl$_2$) δ 8.62 (dd, J=5.0, 1.3 Hz, 1H), 8.37 (dd, J=8.6, 1.3 Hz, 1H), 7.57 (s, 1H), 7.50 (dd, J=8.6, 4.9 Hz, 1H), 1.69 (s, 15H); $^{13}$C NMR (200 MHz, CD$_2$Cl$_2$) δ 164.5, 148.2, 146.7, 135.6, 130.5, 127.6, 123.5, 118.9, 113.1, 85.9, 9.1; IR (cm$^{-1}$) 2920, 1441, 1368, 1193, 974, 745, 656; HRMS (EI) m/z calcd. for C$_{19}$H$_{19}$Cl$_3$IrNO [M]$^+$: 575.0161. found: 575.0164.

[Comparative Example 1] Preparation of Catalyst C

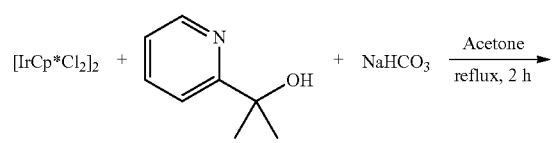

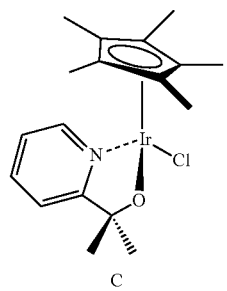

[IrCp*Cl$_2$]$_2$ (Cp*: pentamethylcyclopentadienyl) (0.4106 g, 0.5154 mmol), 2-(2'-pyridyl)-2-propanol (0.1420 g, 1.036 mmol), sodium bicarbonate (0.345 g, 4.11 mmol), and acetone (50 mL) were added to a vial and the mixture was stirred at room temperature for 2 hours. After the reaction was completed, the reactants were filtered with celite (dichloromethane (15 mL×3)), the solvent was removed by distillation under reduced pressure, and separation and purification were performed by column chromatography (n-hexane/acetone=2:1 to 1:1) to prepare Catalyst C.

2-(2'-Pyridyl)-2-Propanol Bound Cp*-Iridium Complex (Catalyst C)

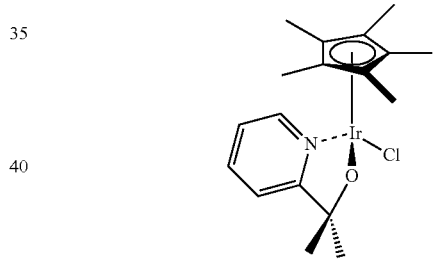

Yellow solid (0.416 g, 81%); $^1$H NMR (400 MHz, MeOD) δ 8.69 (dt, J=5.2, 1.3 Hz, 1H), 7.88 (td, J=7.9, 1.5 Hz, 1H), 7.46-7.31 (m, 2H), 1.67 (s, 15H), 1.46 (s, 6H); $^{13}$C NMR (150 MHz, MeOD) δ 177.34, 150.97, 139.53, 125.54, 122.95, 85.97, 84.74, 33.67, 9.01.

[Comparative Example 2] Preparation of Catalyst D

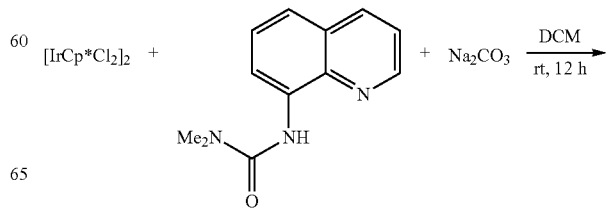

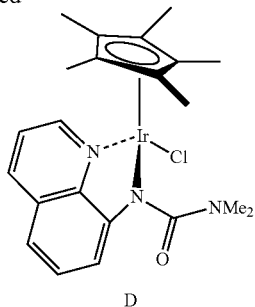

D

[IrCp*Cl$_2$]$_2$ (Cp*: pentamethylcyclopentadienyl) (0.20 g, 0.25 mmol), 8-[N—(N,N-Dimethylaminocarbonyl)amino]quinoline (0.50 mmol), sodium carbonate (0.16 g, 1.50 mmol), and dichloromethane (10 mL) were added to a vial and the mixture stirred at room temperature for 12 hours. After the reaction was completed, the reactants were filtered with celite (dichloromethane (15 mL×3)), the solvent was removed by distillation under reduced pressure, and separation and purification were performed by column chromatography (n-hexane/acetone=2:1 to 1:1) to prepare Catalyst D.

8-[N—(N,N-Dimethylaminocarbonyl)amino]quinoline Bound Cp*-Iridium Complex (Catalyst D)

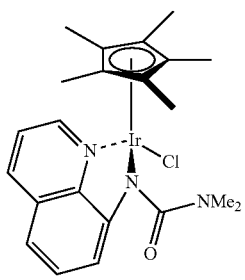

Red solid (0.15 g, 51%); $^1$H NMR (400 MHz, CDCl$_3$) δ 8.47 (d, J=5.0 Hz, 1H), 7.92 (d, J=8.4 Hz, 1H), 7.34-7.28 (m, 2H), 6.93 (d, J=8.0 Hz, 1H), 6.68 (d, J=7.9 Hz, 1H), 3.17 (s, 6H), 1.62 (s, 15H); $^{13}$C NMR (150 MHz, CDCl$_3$, two carbons merged to others) δ 166.5, 154.8, 147.0, 145.0, 137.7, 130.5, 129.9, 121.7, 115.6, 111.6, 86.0 (Cp*), 8.4 (Cp*); IR (cm$^{-1}$) 2910, 1622, 1460, 1358, 1327, 1150, 811, 772; HRMS (EI) m/z calcd. for C$_{22}$H$_{27}$ClIrN$_3$O [M]$^+$: 577.1472. found: 577.1475.

Preparation Example I: Preparation of Hydroxamic Acid

One-Pot Synthesis of Hydroxamic Acids from Carboxylic Acids

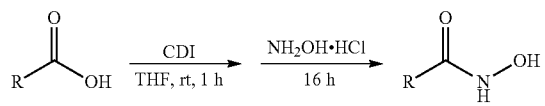

Carboxylic acid (10 mmol) was added to dried tetrahydrofuran (THF, 30 mL), and 1,1'-carbonyldiimidazole (CDI, 15 mmol, 1.5 equiv) was added thereto and the mixture was stirred for 1 hour. Hydroxylamine hydrochloride (1.39 g, 20 mmol) in a powder form was added and the mixture was stirred for 16 hours. After the reaction was completed, the reaction mixture was added to a 5% aqueous KHSO$_4$ solution (30 mL), and extracted with EtOAc (2×30 mL). The collected organic layer was washed with a saline (50 mL), dried with MgSO$_4$, concentrated, and separated and purified by column chromatography (eluent: n-hexane/EtOAc, 1:1 to 1:5) to obtain the desired hydroxamic acid compound.

[Preparation Example 1] Preparation of 2-(3-methoxyphenyl)acetylhydroxamic Acid

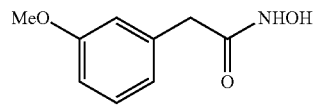

Prepared from 2-(3-methoxyphenyl) acetic acid (10 mmol scale); White solid (1.42 g, 78%); m.p. 115-117° C.; $^1$H NMR (600 MHz, DMSO-d$_6$) δ 10.62 (s, 1H), 8.81 (s, 1H), 7.20 (t, J=7.8 Hz, 1H), 6.86-6.77 (m, 3H), 3.73 (s, 3H), 3.25 (s, 2H); $^{13}$C NMR (150 MHz, DMSO-d$_6$) δ 166.9, 159.1, 137.5, 129.2, 121.2, 114.7, 111.8, 55.0, 39.4; IR (cm$^{-1}$) 3193, 3031, 2895, 1625, 1488, 1256, 1047, 761; HRMS (EI) m/z calcd. for C$_9$H$_{11}$NO$_3$ [M]$^+$: 181.0739. found: 181.0736.

[Preparation Example 2] Preparation of 2-(3,4-dimethoxyphenyl)acetylhydroxamic Acid

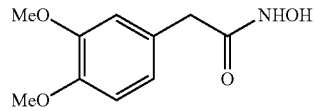

Prepared from 2-(3,4-dimethoxyphenyl)acetic acid (5 mmol scale); White solid (0.57 mg, 54%); m.p. 144-146° C.; $^1$H NMR (600 MHz, DMSO-d$_6$) δ 10.57 (s, 1H), 8.78 (s, 1H), 6.88-6.85 (m, 2H), 6.76 (d, J=8.1 Hz, 1H), 3.73 (s, 3H), 3.71 (s, 3H), 3.20 (s, 2H); $^{13}$C NMR (150 MHz, DMSO-d$_6$) δ 167.2, 148.5, 147.5, 128.4, 120.9, 112.9, 111.8, 55.6, 55.4, 38.9; IR (cm$^{-1}$) 3169, 3010, 1631, 1515, 1259, 1160, 1019, 601; HRMS (EI) m/z calcd. for C$_{10}$H$_{13}$NO$_4$ [M]$^+$: 211.0845. found: 211.0843.

[Preparation Example 3] Preparation of 2-(3-methylphenyl)acetylhydroxamic Acid

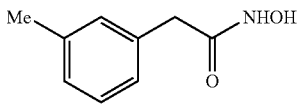

Prepared from 2-(3-methylphenyl)acetic acid (10 mmol scale); White solid (1.17 g, 71%); m.p. 128-130° C.; $^1$H NMR (600 MHz, DMSO-d$_6$) δ 10.63 (s, 1H), 8.81 (s, 1H), 7.17 (t, J=7.5 Hz, 1H), 7.07 (s, 1H), 7.05-7.02 (m, 2H), 3.23

(s, 2H), 2.28 (s, 3H); $^{13}$C NMR (150 MHz, DMSO-d$_6$, one carbon merged to others) δ 167.0, 137.2, 135.9, 129.5, 128.1, 127.0, 126.0, 21.0; IR (cm$^{-1}$) 3159, 3004, 2865, 1628, 1555, 1049, 682, 542; HRMS (EI) m/z calcd. for C$_9$H$_{11}$NO$_2$ [M]$^+$: 165.0790. found: 165.0788.

[Preparation Example 4] Preparation of 2-(3-chlorophenyl)acetylhydroxamic Acid

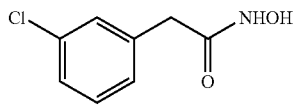

Prepared from 2-(3-chlorophenyl)acetic acid (10 mmol scale); White solid (0.92 g, 50%); m.p. 128-130° C.; $^1$H NMR (600 MHz, DMSO-d$_6$) δ 10.67 (s, 1H), 8.87 (s, 1H), 7.36-7.26 (m, 3H), 7.21 (d, J=7.4 Hz, 1H), 3.30 (s, 2H); $^{13}$C NMR (150 MHz, DMSO-d$_6$) δ 166.4, 138.5, 132.8, 130.0, 128.7, 127.7, 126.4, 38.9; IR (cm$^{-1}$) 3174, 3009, 2897, 1633, 1538, 1052, 617; HRMS (EI) m/z calcd. for C$_8$H$_8$ClNO$_2$ [M]$^+$: 185.0244. found: 185.0241.

[Preparation Example 5] Preparation of 3-phenylpropanyl Hydroxamic Acid

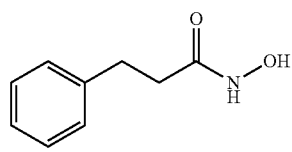 [SMILES: O=C(CCc1ccccc1)NO]

Prepared from 3-phenylpropanoic acid (5.0 mmol scale); White solid (0.75 g, 91%); m.p. 87-89° C.; $^1$H NMR (600 MHz, DMSO-d$_6$) δ 10.38 (s, 1H), 8.72 (s, 1H), 7.27 (t, J=7.5 Hz, 2H), 7.23-7.13 (m, 3H), 2.80 (t, J=7.7 Hz, 2H), 2.25 (t, J=7.7 Hz, 2H); $^{13}$C NMR (150 MHz, DMSO-d$_6$) δ 168.2, 141.1, 128.3, 128.2, 125.9, 33.9, 30.8; IR (cm$^{-1}$) 3285, 2766, 1604, 1059, 694; HRMS (FAB) m/z calcd. for C$_9$H$_{11}$NO$_2$ [M+H]$^+$: 166.0868. found: 166.0869.

[Preparation Example 6] Preparation of 3-(2-bromophenyl)propanyl Hydroxamic Acid

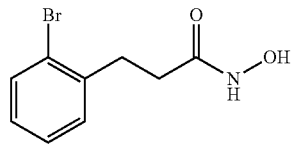 [SMILES: O=C(CCc1ccccc1Br)NO]

Prepared from 3-(2-bromophenyl)propanoic acid (5.0 mmol scale); White solid (1.15 g, 85%); m.p. 104-106° C.; $^1$H NMR (600 MHz, DMSO-d$_6$) δ 10.42 (s, 1H), 8.74 (s, 1H), 7.58 (d, J=7.9 Hz, 1H), 7.34-7.28 (m, 2H), 7.21-7.11 (m, 1H), 2.91 (t, J=7.7 Hz, 2H), 2.27 (t, J=7.7 Hz, 2H); $^{13}$C NMR (150 MHz, DMSO-d$_6$) δ 167.8, 140.0, 132.5, 130.5, 128.3, 127.9, 123.6, 32.1, 31.2; IR (cm$^{-1}$) 3160, 3041, 1618, 1024, 743; HRMS (FAB) m/z calcd. for C$_9$H$_{10}$BrNO$_2$ [M+H]$^+$: 243.9973. found: 243.9975.

[Preparation Example 7] Preparation of 3-(3,4-dimethoxyphenyl)propanoylhydroxamic Acid

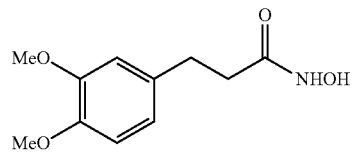

Prepared from 3-(3,4-dimethoxyphenyl)propanoic acid (10 mmol scale); White solid (1.14 g, 50%); m.p. 105-107° C.; $^1$H NMR (600 MHz, DMSO-d$_6$) δ 10.35 (s, 1H), 8.69 (s, 1H), 6.83 (d, J=8.1 Hz, 1H), 6.79 (s, 1H), 6.69 (d, J=8.1 Hz, 1H), 3.73 (s, 3H), 3.70 (s, 3H), 2.74 (t, J=7.7 Hz, 2H), 2.23 (t, J=7.7 Hz, 2H); $^{13}$C NMR (150 MHz, DMSO-d$_6$) δ 168.3, 148.6, 147.1, 133.5, 119.9, 112.2, 111.9, 55.5, 55.4, 34.2, 30.5; IR (cm$^{-1}$) 3191, 3003, 2909, 1631, 1512, 1144, 553; HRMS (EI) m/z calcd. for C$_{11}$H$_{15}$NO$_4$ [M]$^+$: 225.1001. found: 225.1003.

Preparation Example II: Preparation of 3-substituted-1,4,2-dioxazol-5-one Compound A hydroxamic acid compound (5.0 mmol) was dissolved in dichloromethane (50 mL), 1,1' (0.81 g, 5.0 mmol) was added thereto all together at room temperature, and the mixture was stirred for 30 minutes. After the reaction was completed, the product was quenched with 1 N HCl (30 mL), extracted with dichloromethane (50 mL×3), and dried with magnesium sulfate, and the solvent was removed solvent. The residue was filtered with silica and washed with dichloromethane (10 ml×2), and then the filtrate was distilled under reduced pressure to obtain the title compound.

The following compound was prepared in the same manner as in the above, except that the starting material was changed.

[Preparation Example 8] Preparation of 3-(3-ethoxybenzyl)-1,4,2-dioxazol-5-one

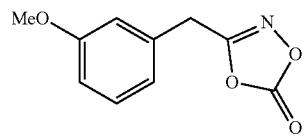 [SMILES: COc1cccc(Cc2noc(=O)o2)c1]

Prepared on a 2 mmol scale; White solid (331 mg, 92%); m.p. 44-46° C.; $^1$H NMR (400 MHz, CDCl$_3$) δ 7.33-7.27 (m, 1H), 6.91-6.86 (m, 2H), 6.83-6.81 (m, 1H), 3.89 (s, 2H), 3.82 (s, 3H); $^{13}$C NMR (100 MHz, CDCl$_3$) δ 165.4, 160.3, 154.0, 131.1, 130.4, 121.3, 114.9, 113.9, 55.5, 31.4; IR (cm$^{-1}$) 3079, 3011, 2842, 1810, 1348, 1147, 986, 745; HRMS (EI) m/z calcd. for C$_{10}$H$_9$NO$_4$ [M]$^+$: 207.0532. found: 207.0532.

[Preparation Example 9] Preparation of 3-(3,4-dimethoxybenzyl)-1,4,2-dioxazol-5-one

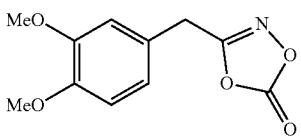 [SMILES: COc1ccc(Cc2noc(=O)o2)cc1OC]

Prepared on a 2 mmol scale; White solid (421 mg, 89%); m.p. 73-75° C.; $^1$H NMR (400 MHz, CDCl$_3$) δ 6.88-6.82 (m, 2H), 6.79-6.76 (m, 1H), 3.89 (s, 3H), 3.88 (s, 3H), 3.87 (s, 2H); $^{13}$C NMR (150 MHz, CDCl$_3$) δ 165.6, 154.1, 149.7, 149.4, 122.7, 121.6, 112.1, 111.9, 56.2, 56.1, 31.0; IR (cm$^{-1}$) 3001, 2929, 2845, 1821, 1511, 1142, 987; HRMS (EI) m/z calcd. for C$_{11}$H$_{11}$NO$_5$ [M]$^+$: 237.0637. found: 237.0639.

[Preparation Example 10] Preparation of 3-(3-methylbenzyl)-1,4,2-dioxazol-5-one

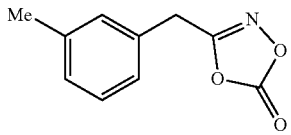 [SMILES: Cc1cccc(Cc2noc(=O)o2)c1]

Prepared on a 2 mmol scale; Colorless liquid (353 mg, 93%); $^1$H NMR (400 MHz, CDCl$_3$) δ 7.3 (t, J=7.6 Hz, 1H), 7.16 (d, J=7.6 Hz, 1H), 7.12-7.04 (m, 2H), 3.87 (s, 2H), 2.36 (s, 3H); $^{13}$C NMR (100 MHz, CDCl$_3$) δ 165.5, 154.1, 139.2, 130.4, 129.8, 129.3, 129.2, 126.1, 31.2, 21.4; IR (cm$^{-1}$) 3022, 2922, 1824, 1349, 1143, 981, 744; HRMS (EI) m/z calcd. for C$_{10}$H$_9$NO$_3$ [M]$^+$: 191.0582. found: 191.0581.

[Preparation Example 11] Preparation of 3-(3-chlorobenzyl)-1,4,2-dioxazol-5-one

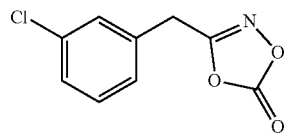 [SMILES: O=c1onc(Cc2cccc(Cl)c2)o1]

Prepared on a 1 mmol scale; White solid (187 mg, 88%); m.p. 49-51° C.; $^1$H NMR (600 MHz, CDCl$_3$) δ 7.37-7.29 (m, 3H), 7.19 (d, J=6.8 Hz, 1H), 3.92 (s, 2H); $^{13}$C NMR (150 MHz, CDCl$_3$) δ 164.8, 153.8, 135.2, 132.3, 130.6, 129.3, 128.9, 127.3, 30.9; IR (cm$^{-1}$) 3064, 2921, 1865, 1831, 1245, 993, 721; HRMS (EI) m/z calcd. for C$_9$H$_6$ClNO$_3$ [M]$^+$: 211.0036. found: 211.0035.

[Preparation Example 12] Preparation of 3-phenethyl-1,4,2-dioxazol-5-one

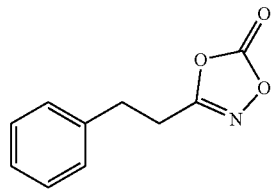 [SMILES: O=c1onc(CCc2ccccc2)o1]

Prepared on a 2.0 mmol scale; White solid (0.36 g, 95%); m.p. 38-40° C.; $^1$H NMR (600 MHz, CDCl$_3$) δ 7.33 (t, J=7.4 Hz, 2H), 7.29-7.23 (m, 1H), 7.19 (d, J=7.4 Hz, 2H), 3.03 (t, J=7.7 Hz, 2H), 2.94 (t, J=7.7 Hz, 2H); $^{13}$C NMR (150 MHz, CDCl$_3$) δ 166.0, 154.1, 138.1, 129.0, 128.3, 127.3, 30.6, 26.8; IR (cm$^{-1}$) 1815, 1636, 1149, 980, 694; HRMS (FAB) m/z calcd. for C$_{10}$H$_9$NO$_3$ [M+H]$^+$: 192.0661. found: 192.0663.

[Preparation Example 13] Preparation of 3-(2-bromophenethyl)-1,4,2-dioxazol-5-one

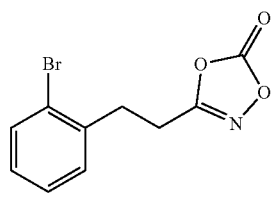 [SMILES: O=c1onc(CCc2ccccc2Br)o1]

Prepared on a 5.0 mmol scale. White solid (1.04 g, 85%); m.p. 71-73° C.; $^1$H NMR (600 MHz, CDCl$_3$) δ 7.6 (d, J=8.0 Hz, 1H), 7.28 (t, J=7.4 Hz, 1H), 7.25 (t, J=6.9 Hz, 1H), 7.15 (t, J=7.4 Hz, 1H), 3.16 (t, J=7.7 Hz, 2H), 2.98 (t, J=7.7 Hz, 2H); $^{13}$C NMR (150 MHz, CDCl$_3$) δ 165.7, 154.1, 137.5, 133.4, 130.6, 129.2, 128.1, 124.3, 31.3, 25.2; IR (cm$^{-1}$) 1862, 1831, 1632, 1150, 755; HRMS (FAB) m/z calcd. for C$_{10}$H$_8$BrNO$_3$ [M+H]$^+$: 269.9766. found: 269.9763.

[Preparation Example 14] Preparation of 3-(3,4-dimethoxyphenethyl)-1,4,2-dioxazol-5-one

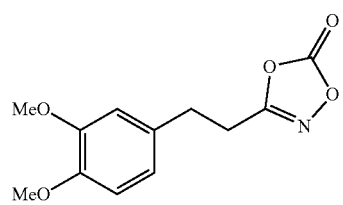 [SMILES: COc1ccc(CCc2noc(=O)o2)cc1OC]

Prepared on a 2 mmol scale; White solid (409 mg, 82%); m.p. 59-61° C.; $^1$H NMR (600 MHz, CDCl$_3$) δ 6.82 (d, J=8.1 Hz, 1H), 6.74 (d, J=8.1 Hz, 1H), 6.70 (s, 1H), 3.87 (s, 3H), 3.86 (s, 3H), 2.98 (t, J=7.1 Hz, 2H), 2.92 (t, J=7.1 Hz, 2H); $^{13}$C NMR (150 MHz, CDCl$_3$) δ 166.0, 154.1, 149.3, 148.3, 130.6, 120.3, 111.7, 111.6, 56.1, 56.0, 30.3, 27.1; IR (cm$^{-1}$) 2962, 2936, 2838, 1821, 1512, 1134, 754; HRMS (EI) m/z calcd. for C$_{12}$H$_{13}$NO$_5$ [M]$^+$: 251.0794. found: 251.0795.

[Preparation Example 15] Preparation of 3-(4-methoxyphenethyl)-1,4,2-dioxazol-5-one

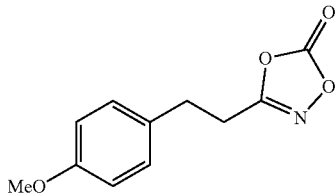 [SMILES: COc1ccc(CCc2noc(=O)o2)cc1]

Prepared on a 2 mmol scale; White solid (420 mg, 95%); m.p. 39-41° C.; $^1$H NMR (600 MHz, CDCl$_3$) δ 7.12 (d, J=8.6 Hz, 2H), 6.86 (d, J=8.6 Hz, 2H), 3.80 (s, 3H), 2.98 (t, J=7.4 Hz, 2H), 2.90 (t, J=7.4 Hz, 2H); $^{13}$C NMR (150 MHz, CDCl$_3$) δ 166.0, 158.8, 154.2, 130.1, 129.4, 114.5, 55.4, 29.8, 27.1; IR (cm$^{-1}$) 3000, 2914, 2834, 1828, 1512, 1222, 750; HRMS (EI) m/z calcd. for C$_{11}$H$_{11}$NO$_4$ [M]$^+$: 221.0688. found: 221.0690.

[Preparation Example 16] Preparation of 3-(4-hydroxyphenethyl)-1,4,2-dioxazol-5-one

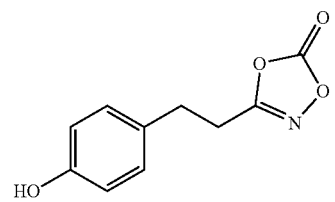

Prepared on 2 mmol scale; White solid (0.20 g, 50%); m.p. 77-79° C.; $^1$H NMR (600 MHz, CDCl$_3$) δ 7.07 (d, J=8.4 Hz, 2H), 6.79 (d, J=8.4 Hz, 2H), 4.84 (br, 1H), 2.97 (t, J=7.5 Hz, 2H), 2.90 (t, J=7.5 Hz, 2H); $^{13}$C NMR (150 MHz, CDCl$_3$) δ 166.0, 154.8, 154.2, 130.3, 129.6, 115.9, 29.9, 27.1; IR (cm$^{-1}$) 3454, 2918, 1810, 1513, 1166, 985, 825; HRMS (EI) m/z calcd. for C$_{10}$H$_9$NO$_4$ [M]$^+$: 207.0532. found: 207.0529.

[Preparation Example 17] Preparation of 3-(4-hydroxy-3-methoxyphenethyl)-1,4,2-dioxazol-5-one

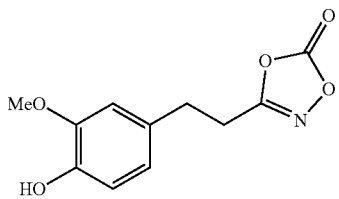 [SMILES: COc1cc(CCc2noc(=O)o2)ccc1O]

Prepared on a 2 mmol scale; White solid (0.19 g, 41%); m.p. 96-98° C.; $^1$H NMR (600 MHz, CDCl$_3$) δ 6.87 (d, J=8.0 Hz, 1H), 6.73-6.64 (m, 2H), 5.55 (s, 1H), 3.88 (s, 3H), 2.99-2.95 (m, 2H), 2.94-2.88 (m, 2H); $^{13}$C NMR (150 MHz, CDCl$_3$) δ 166.0, 154.2, 146.8, 144.9, 130.0, 121.0, 114.9, 110.9, 56.1, 30.4, 27.2; IR (cm$^{-1}$) 3471, 1827, 1510, 1257, 981, 817; HRMS (EI) m/z calcd. for C$_{11}$H$_{11}$NO$_5$ [M]$^+$: 237.0637. found: 237.0635.

[Preparation Example 18] Preparation of 3-(3-bromo-4-hydroxyphenethyl)-1,4,2-dioxazol-5-one

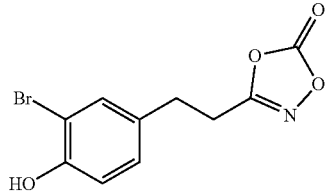 [SMILES: O=c1onc(CCc2ccc(O)c(Br)c2)o1]

Prepared on a 1 mmol scale; White solid (0.07 g, 24%); m.p. 71-73° C.; $^1$H NMR (400 MHz, CDCl$_3$) δ 7.32 (s, 1H), 7.05 (d, J=8.3 Hz, 1H), 6.97 (d, J=8.3 Hz, 1H), 5.51 (s, 1H), 3.45-2.01 (m, 4H); $^{13}$C NMR (150 MHz, CDCl$_3$) δ 165.7, 154.0, 151.6, 131.8, 131.7, 129.2, 116.6, 110.6, 29.4, 26.9; IR (cm$^{-1}$) 3344, 1816, 1649, 1419, 1169, 985, 769; HRMS (EI) m/z calcd. for C$_{10}$H$_8$BrNO$_4$ [M]$^+$: 284.9637. found: 284.9639.

[Preparation Example 19] Preparation of 3-(4-hydroxy-2-methoxyphenethyl)-1,4,2-dioxazol-5-one

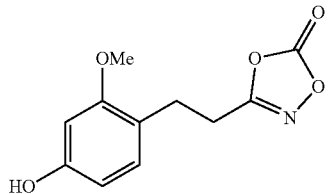 [SMILES: COc1cc(O)ccc1CCc1noc(=O)o1]

Prepared on 1 mmol scale; Colorless oil (0.05 g, 22%); $^1$H NMR (600 MHz, CDCl$_3$) δ 6.93 (d, J=8.1 Hz, 1H), 6.40 (s, 1H), 6.34 (d, J=8.1 Hz, 1H), 3.77 (s, 3H), 2.92 (t, J=7.2 Hz, 2H), 2.85 (t, J=7.2 Hz, 2H); $^{13}$C NMR (150 MHz, CDCl$_3$) δ 166.6, 158.6, 156.4, 154.6, 130.7, 118.5, 107.1, 99.2, 55.4, 25.8, 25.5; IR (cm$^{-1}$) 3333, 2938, 1817, 1596, 1288, 1151, 831; HRMS (EI) m/z calcd. for C$_{11}$H$_{11}$NO$_5$ [M]$^+$: 237.0637. found: 237.0639.

[Preparation Example 20] Preparation of 3-(4-hydroxy-3,5-methoxyphenethyl)-1,4,2-dioxazol-5-one

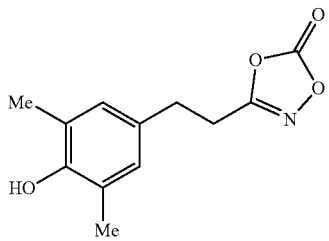 [SMILES: Cc1cc(CCc2noc(=O)o2)cc(C)c1O]

Prepared on a 1 mmol scale; White solid (0.08 g, 36%); m.p. 100-102° C.; $^1$H NMR (600 MHz, CDCl$_3$) δ 6.81 (s, 2H), 4.65 (s, 1H), 2.93-2.85 (m, 4H), 2.23 (s, 6H); $^{13}$C NMR (150 MHz, CDCl$_3$) δ 166.2, 154.3, 151.4, 129.7, 128.4, 123.6, 29.9, 27.1, 16.0; IR (cm$^{-1}$) 3459, 2942, 1861, 1418, 1202, 1149, 984; HRMS (EI) m/z calcd. for C$_{12}$H$_{13}$NO$_4$ [M]$^+$: 235.0845. found: 235.0843.

[Preparation Example 21] Preparation of 2-{2-(4-hydroxyphenyl)-1-(5-oxo-1,4,2-dioxazol-3-yl)ethyl}isoindoline-1,3-dione

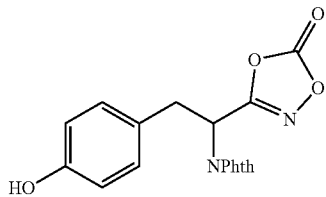

Prepared on 1 mmol scale; White solid (0.11 g, 31%); m.p. 153-155° C.; $^1$H NMR (600 MHz, CDCl$_3$) δ 7.85-7.79 (m, 2H), 7.79-7.70 (m, 2H), 7.05 (d, J=8.2 Hz, 2H), 6.68 (d, J=8.2 Hz, 2H), 5.54 (dd, J=10.2, 5.6 Hz, 1H), 3.63-3.40 (m, 2H); $^{13}$C NMR (150 MHz, CDCl$_3$) δ 166.8, 163.8, 155.2, 153.4, 134.9, 131.2, 130.5, 126.4, 124.1, 115.9, 46.7, 33.1; IR (cm$^{-1}$) 3371, 1855, 1705, 1387, 1310, 991, 711; HRMS (EI) m/z calcd. for C$_{18}$H$_{12}$N$_2$O$_6$ [M]$^+$: 352.0695. found: 352.0699.

[Preparation Example 22] Preparation of 3-(2-hydroxy-4-methoxyphenethyl)-1,4,2-dioxazol-5-one

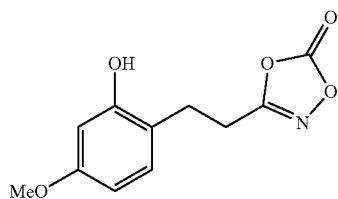 [SMILES: COc1ccc(CCc2noc(=O)o2)c(O)c1]

Prepared on a 1 mmol scale; White solid (0.05 g, 22%); m.p. 59-61° C.; $^1$H NMR (600 MHz, CDCl$_3$) δ 7.00 (d, J=8.3 Hz, 1H), 6.44 (d, J=8.3 Hz, 1H), 6.34 (s, 1H), 5.57 (br, 1H), 3.76 (s, 3H), 2.97 (t, J=6.7 Hz, 2H), 2.92 (t, J=6.7 Hz, 2H); $^{13}$C NMR (150 MHz, CDCl$_3$) δ 166.6, 160.0, 154.7, 154.5, 131.2, 117.2, 106.1, 102.4, 55.5, 25.5, 25.4; IR (cm$^{-1}$) 3417, 2951, 1823, 1521, 1212, 1113, 978; HRMS (EI) m/z calcd. for C$_{11}$H$_{11}$NO$_5$ [M]$^+$: 237.0637. found: 237.0640.

[Preparation Example 23] Preparation of 3-{2-(2-hydroxynaphthalen-1-yl)ethyl}-1,4,2-dioxazol-5-one

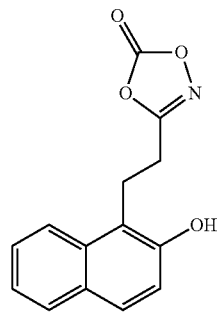 [SMILES: O=c1onc(CCc2c(O)ccc3ccccc23)o1]

Prepared on a 1 mmol scale; Yellow resin (0.07 g, 27%); $^1$H NMR (600 MHz, CDCl$_3$) δ 7.84 (d, J=8.6 Hz, 1H), 7.81 (d, J=8.1 Hz, 1H), 7.69 (d, J=8.8 Hz, 1H), 7.54 (t, J=7.7 Hz, 1H), 7.37 (t, J=7.5 Hz, 1H), 7.03 (d, J=8.8 Hz, 1H), 5.47 (br, 1H), 3.49 (t, J=7.4 Hz, 2H), 2.99 (t, J=7.4 Hz, 2H); $^{13}$C NMR (150 MHz, CDCl$_3$) δ 166.6, 154.5, 151.1, 132.8, 129.6, 129.3, 129.2, 127.4, 123.6, 121.8, 117.8, 116.4, 24.8, 20.4; IR (cm$^{-1}$) 3394, 3065, 1823, 1627, 1513, 1276, 988, 745; HRMS (EI) m/z calcd. for C$_{14}$H$_{11}$NO$_4$ [M]$^+$: 257.0688. found: 257.0689.

[Preparation Example 24] Preparation of 3-(4-hydroxybenzyl)-1,4,2-dioxazol-5-one

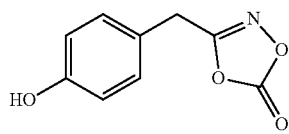

Prepared on a 2 mmol scale; Colorless oil (0.22 g, 56%); $^1$H NMR (600 MHz, CDCl$_3$) δ 7.15 (d, J=8.3 Hz, 2H), 6.83 (d, J=8.3 Hz, 2H), 5.34 (br, 1H), 3.85 (s, 2H); $^{13}$C NMR (150 MHz, CDCl$_3$) δ 165.7, 155.9, 154.2, 130.5, 122.5, 116.3, 30.6; IR (cm$^{-1}$) 3413, 1818, 1513, 1215, 1145, 983, 756; HRMS (EI) m/z calcd. for C$_9$H$_7$NO$_4$ [M]$^+$: 193.0375. found: 193.0371.

[Preparation Example 25] Preparation of 3-{2-(4-methoxy-1H-indol-3-yl)ethyl}-1,4,2-dioxazol-5-one

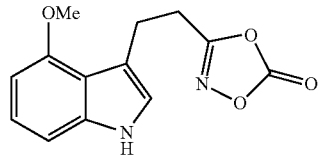 [SMILES: COc1cccc2[nH]cc(CCc3noc(=O)o3)c12]

Prepared on a 1 mmol scale; Pale yellow solid (0.05 g, 26%); m.p. 131-133° C.; $^1$H NMR (600 MHz, CDCl$_3$) δ 7.98 (br, 1H), 7.12 (t, J=8.0 Hz, 1H), 6.98 (d, J=7.9 Hz, 1H), 6.90 (s, 1H), 6.52 (d, J=7.6 Hz, 1H), 3.94 (s, 3H), 3.26 (t, J=6.9 Hz, 2H), 3.05 (t, J=6.9 Hz, 2H); $^{13}$C NMR (150 MHz, CDCl$_3$) δ 166.9, 154.6, 154.5, 138.3, 123.5, 121.0, 116.9, 113.4, 104.8, 99.8, 55.3, 27.4, 22.8; IR (cm$^{-1}$) 3414, 2926, 1812, 1507, 1079, 981, 734; HRMS (EI) m/z calcd. for C$_{13}$H$_{12}$N$_2$O$_4$ [M]$^+$: 260.0797. found: 260.0794.

[Preparation Example 26] Preparation of 3-{2-(1-methyl-1H-indol-3-yl)ethyl}-1,4,2-dioxazol-5-one

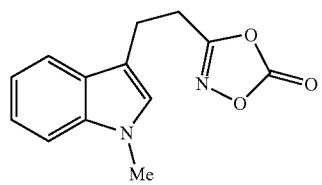 [SMILES: Cn1cc(CCc2noc(=O)o2)c2ccccc21]

Prepared on a 1 mmol scale; Brown solid (0.12 g, 48%); m.p. 78-80° C.; $^1$H NMR (600 MHz, CDCl$_3$) δ 7.55 (d, J=8.0 Hz, 1H), 7.32 (d, J=8.2 Hz, 1H), 7.29-7.24 (m, 1H), 7.15 (t, J=7.5 Hz, 1H), 6.91 (s, 1H), 3.76 (s, 3H), 3.20 (t, J=7.5 Hz, 2H), 3.01 (t, J=7.5 Hz, 2H); $^{13}$C NMR (150 MHz, CDCl$_3$) δ 166.4, 154.3, 137.2, 127.2, 126.8, 122.2, 119.4, 118.4, 111.1, 109.7, 32.8, 26.2, 20.6; IR (cm$^{-1}$) 2926, 1825, 1412, 1328, 1154, 976, 753; HRMS (EI) m/z calcd. for C$_{13}$H$_{12}$N$_2$O$_3$ [M]$^+$: 244.0848. found: 244.0849.

[Preparation Example 27] Preparation of 3-(4-methylphenethyl)-1,4,2-dioxazol-5-one

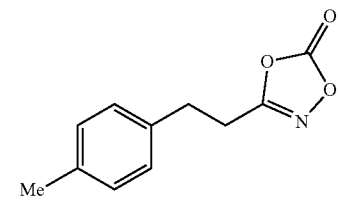

Prepared on a 2 mmol scale; White solid (0.40 g, 97%); m.p. 35-37° C.; $^1$H NMR (600 MHz, CDCl$_3$) δ 7.14 (d, J=7.8 Hz, 2H), 7.09 (d, J=7.8 Hz, 2H), 3.00 (t, J=7.6 Hz, 2H), 2.92 (t, J=7.6 Hz, 2H), 2.34 (s, 3H); $^{13}$C NMR (150 MHz, CDCl$_3$) δ 166.0, 154.2, 136.9, 135.1, 129.7, 128.2, 30.2, 26.9, 21.2; IR (cm$^{-1}$) 2924, 1861, 1815, 1629, 1337, 1147, 984, 788; HRMS (EI) m/z calcd. for C$_{11}$H$_{11}$NO$_3$ [M]$^+$: 205.0739. found: 205.0738.

[Preparation Example 28] Preparation of 3-(4-chlorophenethyl)-1,4,2-dioxazol-5-one

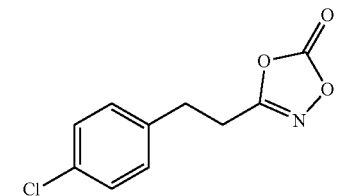 [SMILES: O=c1onc(CCc2ccc(Cl)cc2)o1]

Prepared on a 2 mmol scale; Yellow oil (0.50 g, 98%); $^1$H NMR (600 MHz, CDCl$_3$) δ 7.31 (d, J=8.3 Hz, 2H), 7.14 (d, J=8.3 Hz, 2H), 3.02 (t, J=7.6 Hz, 2H), 2.93 (t, J=7.6 Hz, 2H); $^{13}$C NMR (150 MHz, CDCl$_3$) δ 165.7, 154.0, 136.5, 133.3, 129.7, 129.3, 29.9, 26.7; IR (cm$^{-1}$) 1866, 1823, 1635, 1491, 1091, 978, 758; HRMS (EI) m/z calcd. for C$_{10}$H$_8$ClNO$_3$ [M]$^+$: 225.0193. found: 225.0192.

[Preparation Example 29] Preparation of 3-{4-(trifluoromethyl)phenethyl}-1,4,2-dioxazol-5-one

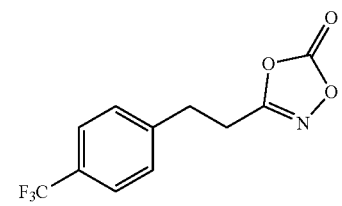 [SMILES: O=c1onc(CCc2ccc(C(F)(F)F)cc2)o1]

Prepared on a 2 mmol scale; Yellow oil (0.32 g, 61%); 1H NMR (600 MHz, CDCl$_3$) δ 7.60 (d, J=7.9 Hz, 2H), 7.34 (d, J=7.9 Hz, 2H), 3.11 (t, J=7.7 Hz, 2H), 2.98 (t, J=7.7 Hz, 2H); $^{13}$C NMR (150 MHz, CDCl$_3$) δ 165.6, 154.0, 142.1, 129.8 (q, J=33.0 Hz), 128.8, 126.1, 124.2 (q, J=271.9 Hz), 30.2, 26.4; $^{19}$F NMR (564 MHz, CDCl$_3$) δ –62.6; IR (cm$^{-1}$) 1868, 1825, 1321, 1107, 979, 825, 760; HRMS (EI) m/z calcd. for C$_{11}$H$_8$F$_3$NO$_3$ [M]$^+$: 259.0456. found: 259.0454.

[Preparation Example 30] Preparation of 3-{2-(4-methoxyphenyl)-2-phenylethyl}-1,4,2-dioxazol-5-one

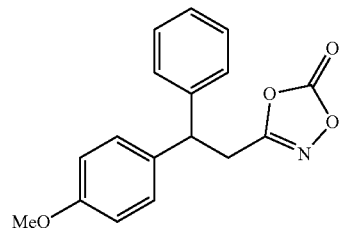 [SMILES: COc1ccc(C(Cc2noc(=O)o2)c2ccccc2)cc1]

Prepared on a 1 mmol scale; Yellow oil (0.28 g, 97%); $^1$H NMR (600 MHz, CDCl$_3$) δ 7.33 (appt, J=7.4 Hz, 2H), 7.28-7.20 (m, 3H), 7.16 (d, J=8.4 Hz, 2H), 6.86 (d, J=8.4 Hz, 2H), 4.43 (t, J=8.2 Hz, 1H), 3.78 (s, 3H), 3.33 (d, J=8.2 Hz, 2H); $^{13}$C NMR (150 MHz, CDCl$_3$) δ 165.2, 158.9, 154.0, 141.8, 133.4, 129.4, 129.1, 128.6, 127.5, 114.5, 55.4, 46.1, 31.5; IR (cm$^{-1}$) 2935, 2836, 1823, 1510, 1246, 979, 698; HRMS (EI) m/z calcd. for C$_{17}$H$_{15}$NO$_4$ [M]$^+$: 297.1001. found: 297.1004.

[Preparation Example 31] Preparation of 3-(2-methylphenethyl)-1,4,2-dioxazol-5-one

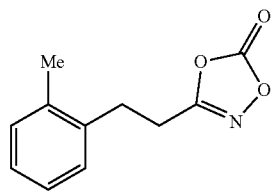

Prepared on a 2 mmol scale; White solid (0.38 g, 92%); m.p. 86-88° C.; $^1$H NMR (600 MHz, CDCl$_3$) δ 7.22-7.06 (m, 4H), 3.04 (t, J=7.8 Hz, 2H), 2.90 (t, J=7.8 Hz, 2H), 2.34 (s, 3H); $^{13}$C NMR (150 MHz, CDCl$_3$) δ 166.1, 154.2, 136.4, 136.0, 130.9, 128.6, 127.5, 126.7, 28.1, 25.6, 19.3; IR (cm$^{-1}$) 3011, 1831, 1605, 1388, 1151, 984, 742; HRMS (EI) m/z calcd. for C$_{11}$H$_{11}$NO$_3$ [M]$^+$: 205.0739. found: 205.0739.

[Preparation Example 32] Preparation of 3-(2,2,2-triphenylethyl)-1,4,2-dioxazol-5-one

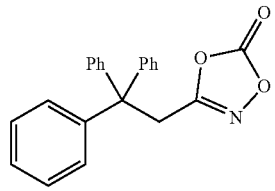 [SMILES: O=c1onc(CC(c2ccccc2)(c2ccccc2)c2ccccc2)o1]

Prepared on a 2 mmol scale; White solid (0.29 g, 43%); m.p. 170-172° C.; 1H NMR (600 MHz, CDCl$_3$) δ 7.40-7.23 (m, 15H), 4.00 (s, 2H); $^{13}$C NMR (150 MHz, CDCl$_3$) δ 165.0, 153.7, 144.8, 128.8, 128.4, 127.1, 56.3, 37.0; IR (cm$^{-1}$) 3056, 1818, 1366, 1149, 977, 697; HRMS (EI) m/z calcd. for C22H$_{17}$NO$_3$ [M]$^+$: 343.1208. found: 343.1212.

[Preparation Example 33] Preparation of 3-{2-(Naphthalen-1-yl)ethyl}-1,4,2-dioxazol-5-one

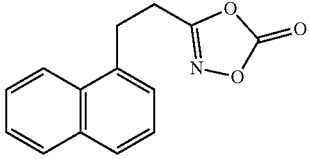 [SMILES: O=c1onc(CCc2cccc3ccccc23)o1]

Prepared on a 2 mmol scale; White solid (0.20 g, 42%); m.p. 78-80° C.; 1H NMR (600 MHz, CDCl$_3$) δ 7.98-7.93 (m, 1H), 7.93-7.88 (m, 1H), 7.83-7.75 (m, 1H), 7.58 (t, J=7.2 Hz, 1H), 7.53 (t, J=7.2 Hz, 1H), 7.43 (t, J=7.6 Hz, 1H), 7.39-7.32 (m, 1H), 3.50 (t, J=7.9 Hz, 2H), 3.07 (t, J=7.9 Hz, 2H); $^{13}$C NMR (150 MHz, CDCl$_3$, one carbon merged to others) δ 166.1, 154.1, 134.2, 131.3, 129.4, 128.3, 126.8, 126.5, 126.1, 125.7, 122.8, 28.0, 26.1; IR (cm$^{-1}$) 3045, 1828, 1633, 1317, 1154, 986, 761; HRMS (EI) m/z calcd. for C$_4$H$_{11}$NO$_3$ [M]$^+$: 241.0739. found: 241.0739.

[Preparation Example 34] Preparation of 3-(4-Methoxybenzyl)-1,4,2-dioxazol-5-one

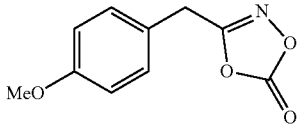 [SMILES: COc1ccc(Cc2noc(=O)o2)cc1]

Prepared on a 1 mmol scale; White solid (0.20 g, 96%); 1H NMR (600 MHz, CDCl$_3$) δ 7.21 (d, J=8.6 Hz, 2H), 6.91 (d, J=8.6 Hz, 2H), 3.87 (s, 2H), 3.81 (s, 3H); $^{13}$C NMR (150 MHz, CDCl$_3$) δ 165.7, 159.8, 154.1, 130.3, 122.3, 114.8, 55.5, 30.6.

[Preparation Example 35] Preparation of 3-(3-methoxyphenethyl)-1,4,2-dioxazol-5-one

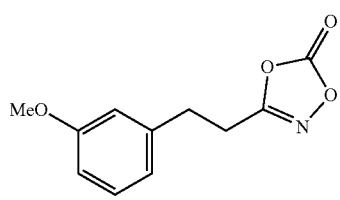 [SMILES: COc1cccc(CCc2noc(=O)o2)c1]

Prepared on a 2 mmol scale; White solid (0.43 g, 97%); m.p. 35-37° C.; $^1$H NMR (600 MHz, CDCl$_3$) δ 7.25 (t, J=7.3 Hz, 1H), 6.84-6.76 (m, 2H), 6.74 (s, 1H), 3.80 (s, 3H), 3.00 (t, J=7.7 Hz, 2H), 2.93 (t, J=7.7 Hz, 2H); $^{13}$C NMR (150 MHz, CDCl$_3$) δ 166.0, 160.1, 154.1, 139.7, 130.1, 120.6, 114.3, 112.5, 55.4, 30.6, 26.7; IR (cm$^{-1}$) 2940, 1826, 1583, 1257, 1151, 982, 782, 693; HRMS (EI) m/z calcd. for C$_{11}$H$_{11}$NO$_4$ [M]$^+$: 221.0688. found: 221.0686.

[Preparation Example 36] Preparation of 3-(3-Bromophenethyl)-1,4,2-dioxazol-5-one

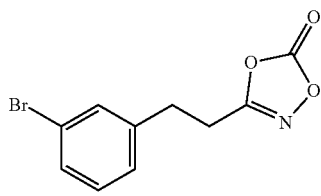 [SMILES: O=c1onc(CCc2cccc(Br)c2)o1]

Prepared on a 2 mmol scale; Colorless oil (0.51 g, 95%); $^1$H NMR (600 MHz, CDCl$_3$) δ 7.41 (d, J=8.0 Hz, 1H), 7.37 (s, 1H), 7.21 (t, J=7.8 Hz, 1H), 7.14 (d, J=7.6 Hz, 1H), 3.02 (t, J=7.6 Hz, 2H), 2.98-2.90 (t, J=7.6 Hz, 2H); $^{13}$C NMR (150 MHz, CDCl$_3$) δ 165.6, 154.0, 140.4, 131.5, 130.6, 130.5, 127.0, 123.1, 30.1, 26.6; IR (cm$^{-1}$) 1866, 1823, 1634, 1145, 978, 757, 684; HRMS (EI) m/z calcd. for C$_{10}$H$_8$BrNO$_3$ [M]$^+$: 268.9688. found: 268.9690.

EXAMPLE II: PREPARATION LACTAM COMPOUND FROM 3-SUBSTITUTED DIOXAZOL-ONE COMPOUND

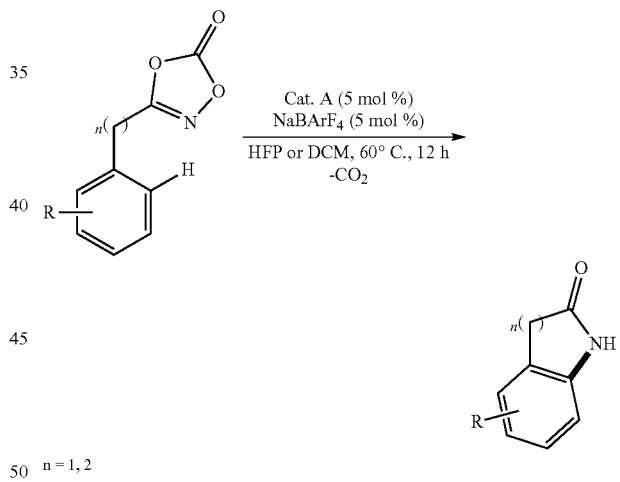

n = 1, 2

An iridium catalyst (Catalyst A, 2.6 mg, 5.0 mol %), sodium tetrakis[3,5-bis(trifluoromethyl)phenyl]borate (NaBAr$^F_4$, 4.43 mg, 5.0 mol %), and hexafluoro-2-propanol (HFP) or dichloromethane (1.2 mL) were added to a well-dried vial under an argon atmosphere, the mixture was stirred for 1 minute, a 3-substituted dioxazol-one compound (0.1 mmol) was added thereto, and the vial was sealed under the argon atmosphere. Thereafter, the reaction mixture was vigorously stirred at 60° C. for 12 hours, cooled to room temperature, filtered with celite, washed with dichloromethane (10 mL×4), and then concentrated under reduced pressure. The concentrated residue was separated and purified with column chromatography (eluent: n-hexane/10% methanol-EtOAc solution, 2:1 to 1:1 or n-hexane/EtOAc, 2:1~1:2) to obtain the desired lactam compound.

[Example 3] Preparation of 5-Methoxyindolin-2-one (1-A)/7-Methoxyindolin-2-one (1-B)

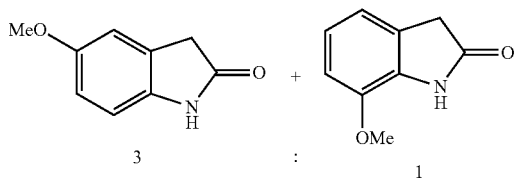 [SMILES: COc1ccc2c(c1)CC(=O)N2 ; COc1cccc2c1NC(=O)C2]

3 : 1

DCM (1.2 mL) was used as a solvent, and the reaction was performed at room temperature. White solid (15 mg, 90%); a mixture of two isomers at a ratio of 3.0:1 was obtained.

Major isomer (5-Methoxyindolin-2-one (1-A)) White solid; 1H NMR (600 MHz, CDCl$_3$) δ 7.90 (s, 1H), 6.85 (s, 1H), 6.80-6.72 (m, 2H), 3.78 (s, 3H), 3.52 (s, 2H); $^{13}$C NMR (150 MHz, CDCl$_3$) δ 177.1, 155.9, 135.9, 126.8, 112.7, 112.0, 110.0, 56.0, 36.7.

Minor isomer (7-Methoxyindolin-2-one (1-B)): White solid; $^1$H NMR (600 MHz, CDCl$_3$) δ 7.64 (s, 1H), 6.98 (t, J=7.9 Hz, 1H), 6.85 (d, J=7.4 Hz, 1H), 6.81 (d, J=8.2 Hz, 1H), 3.87 (s, 3H), 3.55 (s, 2H); $^{13}$C NMR (150 MHz, CDCl$_3$) δ 176.4, 143.8, 131.3, 126.1, 122.9, 117.1, 110.3, 55.8, 36.8.

[Example 4] Preparation of 5,6-dimethoxyindolin-2-one (2)

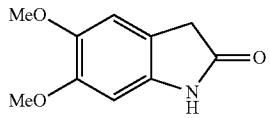

HFP (1.2 mL) was used as a solvent. White solid (18 mg, 93%); $^1$H NMR (600 MHz, CDCl$_3$) δ 8.60 (s, 1H), 6.84 (s, 1H), 6.54 (s, 1H), 3.86 (s, 3H), 3.84 (s, 3H), 3.50 (s, 2H); $^{13}$C NMR (100 MHz, CDCl$_3$) δ 178.5, 149.5, 145.1, 136.2, 116.0, 109.8, 95.8, 57.0, 56.4, 36.6.

[Example 5] Preparation of 5-methylindolin-2-one (3-A)/7-methylindolin-2-one (3-B)

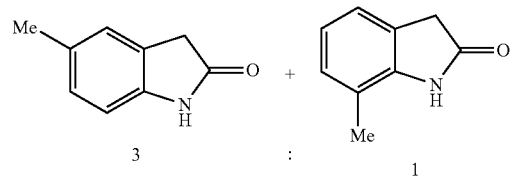 [SMILES: Cc1ccc2c(c1)CC(=O)N2 ; Cc1cccc2c1NC(=O)C2]

3 : 1

HFP (1.2 mL) was used as a solvent. White solid (8 mg, 55%); a mixture of two isomers at a ratio of 3.0:1 was obtained, and regioselectivity was determined from $^1$H NMR of the mixture in which regioisomers are mixed.

Major isomer (5-Methylindolin-2-one (3-A)): $^1$H NMR (600 MHz, CDCl$_3$) δ 8.09 (s, 1H), 7.12-6.98 (m, 2H), 6.76 (d, J=7.8 Hz, 1H), 3.50 (s, 2H), 2.32 (s, 3H); $^{13}$C NMR (150 MHz, CDCl$_3$) δ 177.9, 140.1, 132.0, 128.3, 125.6, 125.5, 109.5, 36.4, 21.2.

Minor isomer (7-methylindolin-2-one (3-B)): $^1$H NMR (600 MHz, CDCl$_3$) δ 8.55 (s, 1H), 7.12-6.98 (m, 2H), 6.94 (t, J=7.5 Hz, 1H), 3.56 (s, 2H), 2.28 (s, 3H); $^{13}$C NMR (150 MHz, CDCl$_3$) δ 178.4, 141.6, 129.3, 125.0, 122.4, 122.1, 119.4, 36.8, 16.6.

[Example 6] Preparation of 5-chloroindolin-2-one (4-A)/7-chloroindolin-2-one (4-B)

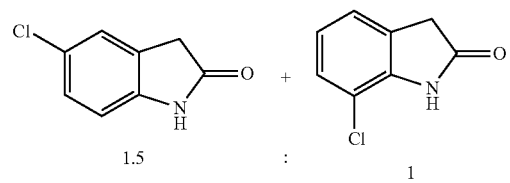 [SMILES: O=C1Cc2cc(Cl)ccc2N1 ; O=C1Cc2cccc(Cl)c2N1]

1.5 : 1

HFP (1.2 mL) was used as a solvent. White solid (7 mg, 40%); a mixture of two isomers at a ratio of 1.5:1 was obtained.

Major isomer (5-Chloroindolin-2-one (4-A)) White solid; $^1$H NMR (600 MHz, CDCl$_3$) δ 8.31 (s, 1H), 7.23-7.19 (m, 2H), 6.80 (d, J=8.1 Hz, 1H), 3.54 (s, 2H); $^{13}$C NMR (150 MHz, CDCl$_3$) δ 176.9, 141.0, 128.1, 127.9, 127.0, 125.3, 110.6, 36.3.

Minor isomer (7-Chloroindolin-2-one (4-B)): White solid; $^1$H NMR (400 MHz, CDCl$_3$) δ 7.87 (s, 1H), 7.21 (d, J=8.6 Hz, 1H), 7.12 (d, J=6.8 Hz, 1H), 6.97 (t, J=7.8 Hz, 1H), 3.62 (s, 2H); $^{13}$C NMR (150 MHz, CDCl$_3$) δ 175.5, 140.0, 127.8, 126.4, 123.2, 122.9, 114.7, 36.9.

[Example 7] Preparation of 6,7-dimethoxy-3,4-dihydroquinolin-2(1H)-one (5)

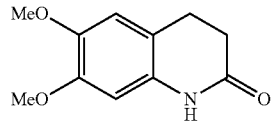

HFP (1.2 mL) was used as a solvent. White solid (20 mg, 96%); $^1$H NMR (600 MHz, CDCl$_3$) δ 9.01 (s, 1H), 6.67 (s, 1H), 6.41 (s, 1H), 3.85 (s, 3H), 3.84 (s, 3H), 2.88 (t, J=7.6 Hz, 2H), 2.61 (t, J=7.6 Hz, 2H); $^{13}$C NMR (150 MHz, CDCl$_3$) δ 172.1, 148.6, 144.9, 130.8, 115.0, 111.8, 100.6, 56.5, 56.3, 31.1, 25.2.

EXAMPLE III: PREPARATION OF LACTAM COMPOUND FROM 3-SUBSTITUTED DIOXAZOL-ONE COMPOUND

An iridium catalyst (Catalyst B, 2.9 mg, 5.0 mol %), sodium tetrakis[3,5-bis(trifluoromethyl)phenyl]borate (4.43 mg, 5.0 mol %), and hexafluoro-2-propanol (1.2 mL) were added to a well-dried vial under an argon atmosphere, the mixture was stirred for 1 minute, a 3-substituted dioxazol-one compound (0.1 mmol) was added, and the vial was sealed under the argon atmosphere. Thereafter, the reaction mixture was vigorously stirred at 60° C. for 12 hours, cooled to room temperature, filtered with celite, washed with dichloromethane (10 mL×4), and then concentrated under reduced pressure. The concentrated residue was separated and purified with column chromatography (eluent:

n-hexane/10% methanol-EtOAc solution, 2:1 to 1:1 or n-hexane/EtOAc, 2:1~1:2) to obtain the desired lactam compound.

[Example 8] Preparation of 6-methoxy-3,4-dihydro-quinolin-2(1H)-one (6)

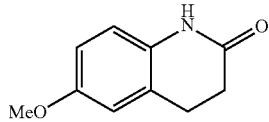

White solid (18 mg, 99%); m.p. 140-142° C.; $^1$H NMR (600 MHz, CDCl$_3$) δ 9.08 (s, 1H), 6.76 (d, J=8.1 Hz, 1H), 6.73-6.68 (m, 2H), 3.77 (s, 3H), 2.93 (t, J=7.5 Hz, 2H), 2.61 (t, J=7.5 Hz, 2H); $^{13}$C NMR (150 MHz, CDCl$_3$) δ 171.8, 155.7, 131.0, 125.1, 116.4, 114.0, 112.6, 55.7, 30.8, 25.8; IR (cm$^{-1}$) 3191, 3054, 2934, 1660, 1499, 1240, 793; HRMS (EI) m/z calcd. for C$_{10}$H$_{11}$NO$_2$ [M]$^+$: 177.0790. found: 177.0791.

[Example 9] Preparation of 3,4-dihydroquinolin-2(1H)-one (7)

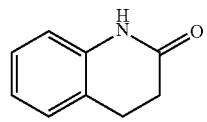 [SMILES: O=C1CCc2ccccc2N1]

White solid (14 mg, 95%); $^1$H NMR (600 MHz, CDCl$_3$) δ 9.08 (s, 1H), 7.21-7.09 (m, 2H), 6.98 (t, J=7.3 Hz, 1H), 6.84 (d, J=7.7 Hz, 1H), 2.97 (t, J=7.5 Hz, 2H), 2.65 (t, J=7.5 Hz, 2H); $^{13}$C NMR (150 MHz, CDCl$_3$) δ 172.3, 137.4, 128.0, 127.7, 123.8, 123.2, 115.6, 30.9, 25.5.

[Example 10] Preparation of 6-methyl-3,4-dihydro-quinolin-2(1H)-one (8)

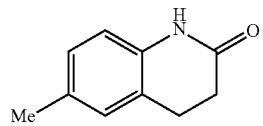 [SMILES: Cc1ccc2c(c1)CCC(=O)N2]

White solid (14 mg, 88%); m.p. 128-130° C.; 1H NMR (600 MHz, CDCl$_3$) δ 8.86 (s, 1H), 7.08-6.87 (m, 2H), 6.72 (d, J=8.3 Hz, 1H), 2.92 (t, J=7.5 Hz, 2H), 2.62 (t, J=7.5 Hz, 2H), 2.29 (s, 3H); $^{13}$C NMR (150 MHz, CDCl$_3$) δ 172.1, 134.9, 132.8, 128.7, 128.1, 123.7, 115.5, 30.9, 25.5, 20.9; IR (cm$^{-1}$) 3189, 3051, 2918, 1667, 1504, 1373, 812; HRMS (EI) m/z calcd. for C$_{10}$H$_{11}$NO [M]$^+$: 161.0841. found: 161.0838.

[Example 11] Preparation of 6-chloro-3,4-dihydro-quinolin-2(1H)-one (9)

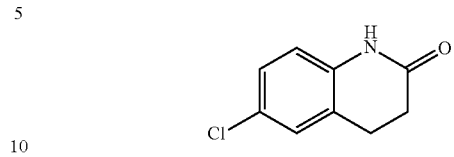

White solid (17 mg, 94%); m.p. 158-160° C.; $^1$H NMR (600 MHz, CDCl$_3$) δ 9.25 (s, 1H), 7.19-7.08 (m, 2H), 6.77 (d, J=8.0 Hz, 1H), 2.95 (t, J=7.6 Hz, 2H), 2.63 (t, J=7.6 Hz, 2H); $^{13}$C NMR (150 MHz, CDCl$_3$) δ 172.0, 136.1, 128.2, 128.1, 127.6, 125.4, 116.8, 30.5, 25.4; IR (cm$^{-1}$) 3193, 3051, 2895, 1669, 1406, 1186, 808; HRMS (EI) m/z calcd. for C$_9$H$_8$ClNO [M]$^+$: 181.0294. found: 181.0298.

[Example 12] Preparation of 6-methoxy-4-phenyl-3,4-dihydroquinolin-2(1H)-one (10)

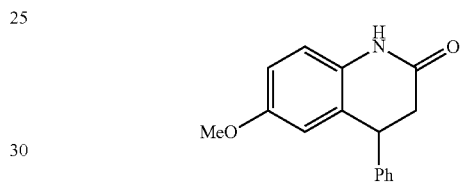

White solid (25 mg, 99%); m.p. 122-124° C.; 1H NMR (600 MHz, CDCl$_3$) δ 9.55 (s, 1H), 7.32 (t, J=7.5 Hz, 2H), 7.28-7.21 (m, 1H), 7.18 (d, J=7.3 Hz, 2H), 6.85 (d, J=8.6 Hz, 1H), 6.72 (d, J=8.6 Hz, 1H), 6.46 (s, 1H), 4.24 (t, J=7.3 Hz, 1H), 3.67 (s, 3H), 2.98-2.83 (m, 2H); $^{13}$C NMR (150 MHz, CDCl$_3$) δ 170.9, 155.9, 141.5, 130.9, 129.1, 128.2, 127.9, 127.4, 116.8, 114.5, 112.9, 55.6, 42.4, 38.5; IR (cm$^{-1}$) 3208, 3082, 1681, 1492, 1258, 1096, 701; HRMS (EI) m/z calcd. for C$_{16}$H$_{15}$NO$_2$ [M]$^+$: 253.1103. found: 253.1099.

[Example 13] Preparation of 5-methyl-3,4-dihydro-quinolin-2(1H)-one (11-A)/8-Methyl-3,4-dihydro-quinolin-2(1H)-one (11-B)

White solid (11 mg, 71%); a mixture of two isomers at a ratio of 1.2:1 was obtained.

Major isomer (5-Methyl-3,4-dihydroquinolin-2(1H)-one (11-A)): White solid; m.p. 160-162° C.; $^1$H NMR (600 MHz, CDCl$_3$) δ 8.18 (s, 1H), 7.07 (t, J=7.6 Hz, 1H), 6.87 (d, J=7.5 Hz, 1H), 6.63 (d, J=7.8 Hz, 1H), 2.91 (t, J=7.6 Hz, 2H), 2.64 (t, J=7.6 Hz, 2H), 2.29 (s, 3H); $^{13}$C NMR (150 MHz, CDCl$_3$) δ 171.5, 137.3, 136.3, 127.3, 125.2, 122.2, 113.5, 30.5, 22.1, 19.5; IR (cm$^{-1}$) 3140, 2915, 1672, 1390, 1218, 766; HRMS (EI) m/z calcd. for C$_{10}$H$_{11}$NO [M]$^+$: 161.0841. found: 161.0843.

Minor isomer (8-Methyl-3,4-dihydroquinolin-2(1H)-one (11-B)): White solid; m.p. 132-134° C.; $^1$H NMR (600 MHz, CDCl$_3$) δ 7.58 (s, 1H), 7.08-7.00 (m, 2H), 6.91 (t, J=7.5 Hz, 1H), 2.96 (t, J=7.5 Hz, 2H), 2.63 (t, J=7.5 Hz, 2H), 2.23 (s, 3H); $^{13}$C NMR (150 MHz, CDCl$_3$) δ 171.6, 135.6, 129.2, 126.0, 123.8, 122.9, 122.8, 30.9, 25.8, 16.8; IR (cm$^{-1}$) 3233, 2848, 1659, 1381, 1191, 729; HRMS (EI) m/z calcd. for C$_{10}$H$_{11}$NO [M]$^+$: 161.0841. found: 161.0839.

[Example 14] Preparation of 4,4-diphenyl-3,4-dihydroquinolin-2(1H)-one (12)

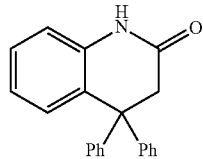 [SMILES: O=C1CC(c2ccccc2)(c2ccccc2)c2ccccc2N1]

White solid (29 mg, 97%); m.p. 253-255° C.; $^1$H NMR (600 MHz, CDCl$_3$) δ 8.40 (s, 1H), 7.43-7.17 (m, 7H), 7.11-7.02 (m, 4H), 6.99 (t, J=7.5 Hz, 1H), 6.89-6.78 (m, 2H), 3.40 (s, 2H); $^{13}$C NMR (150 MHz, CDCl$_3$) δ 170.3, 143.8, 137.1, 131.4, 129.6, 128.7, 128.5, 128.3, 127.2, 123.2, 116.3, 52.0, 44.6; IR (cm$^{-1}$) 3065, 2911, 1674, 1485, 1372, 757, 697; HRMS (EI) m/z calcd. for C$_{21}$H$_{17}$NO [M]$^+$: 299.1310. found: 299.1313.

[Example 15] Preparation of 3,4-dihydrobenzo[h]quinolin-2(1H)-one (13)

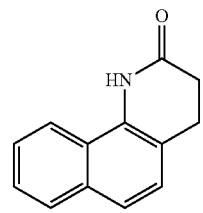 [SMILES: O=C1CCc2ccc3ccccc3c2N1]

Brown solid (18 mg, 93%); m.p. 193-195° C.; $^1$H NMR (600 MHz, CDCl$_3$) δ 8.94 (s, 1H), 7.93 (d, J=8.5 Hz, 1H), 7.84 (d, J=8.1 Hz, 1H), 7.59-7.51 (m, 2H), 7.49 (t, J=7.5 Hz, 1H), 7.30 (d, J=8.2 Hz, 1H), 3.13 (t, J=7.6 Hz, 2H), 2.78 (t, J=7.6 Hz, 2H); $^{13}$C NMR (150 MHz, CDCl$_3$) δ 172.1, 133.2, 132.1, 128.8, 126.6, 126.2, 125.9, 123.1, 122.5, 119.6, 119.4, 31.1, 26.1; IR (cm$^{-1}$) 3216, 2928, 1660, 1469, 1392, 816, 758; HRMS (EI) m/z calcd. for C$_{13}$H$_{11}$NO [M]$^+$: 197.0841. found: 197.0842.

[Example 16] Preparation of 8-bromo-3,4-dihydroquinolin-2(1H)-one (14)

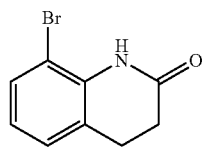 [SMILES: O=C1CCc2cccc(Br)c2N1]

White solid (17 mg, 75%); m.p. 77-79° C.; 1H NMR (600 MHz, CDCl$_3$) δ 7.80 (s, 1H), 7.40 (d, J=8.1 Hz, 1H), 7.12 (d, J=7.3 Hz, 1H), 6.87 (t, J=7.7 Hz, 1H), 2.99 (t, J=7.5 Hz, 2H), 2.64 (t, J=7.5 Hz, 2H); $^{13}$C NMR (150 MHz, CDCl$_3$) δ 170.7, 135.3, 131.0, 127.3, 125.7, 123.9, 109.8, 30.8, 26.1; IR (cm$^{-1}$) 3185, 2915, 1674, 1467, 1193, 743; HRMS (EI) m/z calcd. for C$_9$H$_8$BrNO [M]$^+$: 224.9789. found: 224.9786.

[Example 17] Preparation of 5-methoxyindolin-2-one (15)

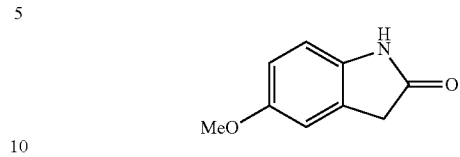

White solid (9 mg, 56%); $^1$H NMR (600 MHz, CD$_2$Cl$_2$) δ 8.15 (s, 1H), 6.86 (s, 1H), 6.79 (d, J=8.4 Hz, 1H), 6.75 (d, J=8.4 Hz, 1H), 3.77 (s, 3H), 3.50 (s, 2H); $^{13}$C NMR (150 MHz, CDCl$_3$) δ 176.7, 155.6, 136.0, 126.8, 112.3, 111.7, 109.6, 55.6, 36.5.

[Example 18] Preparation of 6-methoxy-3,4-dihydroquinolin-2(1H)-one (16-A)/8-Methoxy-3,4-dihydroquinolin-2(1H)-one (16-B)

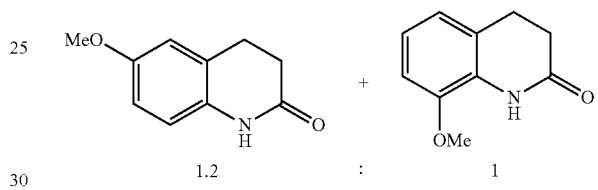

1.2 : 1

White solid (18 mg, 99%); a mixture of two isomers at a ratio of 1.2:1 was obtained.

Major isomer (6-Methoxy-3,4-dihydroquinolin-2(1H)-one (16-A)): White solid; m.p. 140-142° C.; $^1$H NMR (600 MHz, CDCl$_3$) δ 9.08 (s, 1H), 6.76 (d, J=8.1 Hz, 1H), 6.73-6.68 (m, 2H), 3.77 (s, 3H), 2.93 (t, J=7.5 Hz, 2H), 2.61 (t, J=7.5 Hz, 2H); $^{13}$C NMR (150 MHz, CDCl$_3$) δ 171.8, 155.7, 131.0, 125.1, 116.4, 114.0, 112.6, 55.7, 30.8, 25.8; IR (cm$^{-1}$) 3191, 3054, 2934, 1660, 1499, 1240, 793; HRMS (EI) m/z calcd. for C$_{10}$H$_{11}$NO$_2$ [M]$^+$: 177.0790. found: 177.0791.

Minor isomer (8-Methoxy-3,4-dihydroquinolin-2(1H)-one (16-B)): White solid; m.p. 96-98° C.; $^1$H NMR (400 MHz, CDCl$_3$) δ 7.78 (s, 1H), 6.94 (t, J=7.9 Hz, 1H), 6.84-6.62 (m, 2H), 3.86 (s, 3H), 2.96 (t, J=7.6 Hz, 2H), 2.64 (t, J=7.6 Hz, 2H); $^{13}$C NMR (100 MHz, CDCl$_3$) δ 170.5, 145.9, 126.6, 124.1, 122.8, 120.1, 109.1, 55.9, 30.8, 25.5; IR (cm$^{-1}$) 3204, 2953, 1666, 1377, 1261, 1092, 760; HRMS (EI) m/z calcd. for C$_{10}$H$_{11}$NO$_2$ [M]$^+$: 177.0790. found: 177.0788.

[Example 19] Preparation of 6-bromo-3,4-dihydroquinolin-2(1H)-one (17-A)/8-Bromo-3,4-dihydroquinolin-2(1H)-one (17-B)

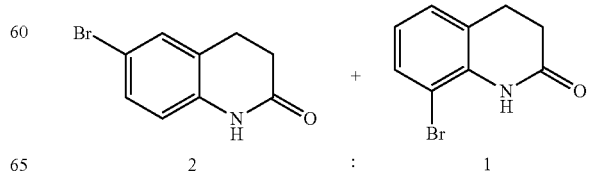

2 : 1

White solid (12 mg, 55%); a mixture of two isomers at a ratio of 2:1 was obtained.

Major isomer (6-Bromo-3,4-dihydroquinolin-2(1H)-one (17-A)): White solid; m.p. 156-158° C.; $^1$H NMR (600 MHz, CDCl$_3$) δ 8.41 (s, 1H), 7.33-7.27 (m, 2H), 6.67 (d, J=8.3 Hz, 1H), 2.95 (t, J=7.5 Hz, 2H), 2.59 (t, J=7.5 Hz, 2H); $^{13}$C NMR (150 MHz, CDCl$_3$) δ 171.3, 136.5, 131.0, 130.6, 125.9, 116.9, 115.6, 30.5, 25.3; IR (cm$^{-1}$) 3050, 2895, 1669, 1487, 1250, 811, 542; HRMS (EI) m/z calcd. for C$_9$H$_8$BrNO [M]$^+$: 224.9789. found: 224.9787.

Minor isomer (8-Bromo-3,4-dihydroquinolin-2(1H)-one (17-B)): White solid; m.p. 77-79° C.; $^1$H NMR (600 MHz, CDCl$_3$) δ 7.80 (s, 1H), 7.40 (d, J=8.1 Hz, 1H), 7.12 (d, J=7.3 Hz, 1H), 6.87 (t, J=7.7 Hz, 1H), 2.99 (t, J=7.5 Hz, 2H), 2.64 (t, J=7.5 Hz, 2H); $^{13}$C NMR (150 MHz, CDCl$_3$) δ 170.7, 135.3, 131.0, 127.3, 125.7, 123.9, 109.8, 30.8, 26.1; IR (cm$^{-1}$) 3185, 2915, 1674, 1467, 1193, 743; HRMS (EI) m/z calcd. for C$_9$H$_8$BrNO [M]$^+$: 224.9789. found: 224.9786.

[Example 20] Preparation of 1-azaspiro[4.5]deca-6,9-diene-2,8-dione (18)

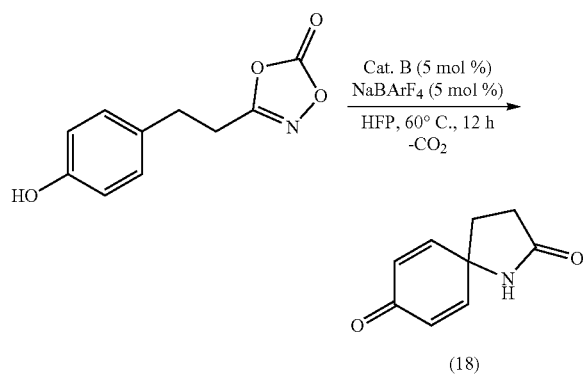

An iridium catalyst (Catalyst B, 2.9 mg, 5.0 mol %), sodium tetrakis[3,5-bis(trifluoromethyl)phenyl]borate (4.43 mg, 5.0 mol %), and hexafluoro-2-propanol (1.2 mL) were added to a well-dried vial under an argon atmosphere, stirred for 1 minute, 3-(4-Hydroxyphenethyl)-1,4,2-dioxazol-5-one (0.1 mmol) was added, and the vial was sealed under the argon atmosphere. Thereafter, the reaction mixture was vigorously stirred at 60° C. for 12 hours, cooled to room temperature, filtered with celite, washed with dichloromethane (10 mL×4), and then concentrated under reduced pressure. The concentrated residue was separated and purified with column chromatography (eluent: n-hexane/EtOAc, 2:1 to 1:2) to obtain 1-azaspiro[4.5]deca-6,9-diene-2,8-dione (18).

1-Azaspiro[4.5]deca-6,9-diene-2,8-dione (18)

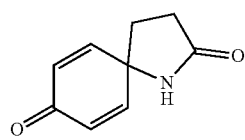

White solid (16 mg, 98%); m.p. 166-158° C.; $^1$H NMR (600 MHz, acetone-d$_6$) δ 7.04 (d, J=9.7 Hz, 2H), 6.12 (d, J=9.7 Hz, 2H), 2.45 (t, J=8.0 Hz, 2H), 2.27 (t, J=8.0 Hz, 2H); $^{13}$C NMR (150 MHz, acetone-d$_6$, one carbon merged to others) δ 185.0, 177.0, 151.8, 128.5, 57.9, 32.8; IR (cm$^{-1}$) 3246, 1696, 1618, 1247, 859, 682; HRMS (EI) m/z calcd. for C$_9$H$_9$NO$_2$ [M]$^+$: 163.0633. found: 163.0633.

[Example 21] Preparation of 7-methoxy-1-azaspiro[4.5]deca-6,9-diene-2,8-dione (19)

7-Methoxy-1-azaspiro[4.5]deca-6,9-diene-2,8-dione (19) was prepared in the same manner as in Example 20, except that 3-(4-Hydroxy-3-methoxyphenethyl)-1,4,2-dioxazol-5-one (0.1 mmol) was used as a starting material instead of 3-(4-Hydroxyphenethyl)-1,4,2-dioxazol-5-one.

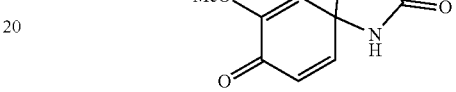

White solid (19 mg, 99%); m.p. 221-223° C.; $^1$H NMR (600 MHz, CDCl$_3$) δ 6.84 (d, J=9.9 Hz, 1H), 6.23 (d, J=10.8 Hz, 1H), 6.16 (s, 1H), 5.71 (s, 1H), 3.68 (s, 3H), 2.60-2.52 (m, 2H), 2.38-2.24 (m, 2H); $^{13}$C NMR (150 MHz, CDCl$_3$) δ 180.0, 177.1, 150.8, 150.0, 127.9, 116.7, 59.1, 55.2, 33.6, 29.7; IR (cm$^{-1}$) 3301, 1671, 1640, 1395, 1209, 1109, 864; HRMS (EI) m/z calcd. for C$_{10}$H$_{11}$NO$_3$ [M]$^+$: 193.0739. found: 193.0739.

[Example 22] Preparation of 7-bromo-1-azaspiro[4.5]deca-6,9-diene-2,8-dione (20)

7-Bromo-1-azaspiro[4.5]deca-6,9-diene-2,8-dione (20) was prepared in the same manner as in Example 20, except that 3-(3-bromo-4-hydroxyphenethyl)-1,4,2-dioxazol-5-one (0.1 mmol) was used as a starting material instead of 3-(4-hydroxyphenethyl)-1,4,2-dioxazol-5-one.

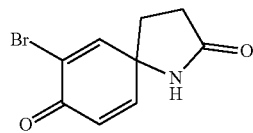

White solid (23 mg, 95%); m.p. 187-189° C.; 1H NMR (600 MHz, CDCl$_3$) δ 7.29 (s, 1H), 6.86 (d, J=9.9 Hz, 1H), 6.70 (s, 1H), 6.34 (d, J=9.9 Hz, 1H), 2.62-2.47 (m, 2H), 2.37-2.25 (m, 2H); $^{13}$C NMR (150 MHz, CDCl$_3$) δ 177.5, 177.2, 149.7, 149.6, 127.3, 124.9, 60.3, 32.1, 29.3; IR (cm$^{-1}$) 3144, 3053, 2854, 1667, 1334, 1098, 798, 665; HRMS (EI) m/z calcd. for C$_9$H$_8$BrNO$_2$ [M+H]$^+$: 241.9817. found: 241.9815.

[Example 23] Preparation of 6-methoxy-1-azaspiro[4.5]deca-6,9-diene-2,8-dione (21)

6-Methoxy-1-azaspiro[4.5]deca-6,9-diene-2,8-dione (21) was prepared in the same manner as in Example 20, except that 3-(4-hydroxy-2-methoxyphenethyl)-1,4,2-dioxazol-5-one (0.1 mmol) was used as a starting material instead of 3-(4-hydroxyphenethyl)-1,4,2-dioxazol-5-one.

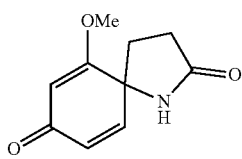

White solid (19 mg, 99%); m.p. 179-181° C.; 1H NMR (600 MHz, CDCl$_3$) δ 6.84 (d, J=9.9 Hz, 1H), 6.23 (d, J=10.8 Hz, 1H), 6.16 (s, 1H), 5.71 (s, 1H), 3.68 (s, 3H), 2.60-2.52 (m, 2H), 2.38-2.24 (m, 2H); $^{13}$C NMR (150 MHz, CDCl$_3$) δ 180.0, 177.1, 150.8, 150.0, 127.9, 116.7, 59.1, 55.2, 33.6, 29.7; IR (cm$^{-1}$) 3144, 3067, 2875, 1664, 1224, 855, 511; HRMS (EI) m/z calcd. for C$_{10}$H$_{11}$NO$_3$ [M]$^+$: 193.0739. found: 193.0741.

[Example 24] Preparation of 7,9-dimethyl-1-azaspiro[4.5]deca-6,9-diene-2,8-dione (22)

7,9-Dimethyl-1-azaspiro[4.5]deca-6,9-diene-2,8-dione (22) was prepared in the same manner as in Example 20, except that 3-(4-hydroxy-3,5-dimethylphenethyl)-1,4,2-dioxazol-5-one (0.1 mmol) was used as a starting material instead of 3-(4-hydroxyphenethyl)-1,4,2-dioxazol-5-one.

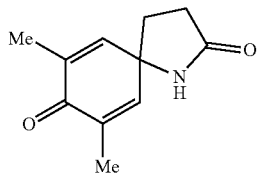

White solid (18 mg, 93%); m.p. 183-185° C.; $^1$H NMR (600 MHz, CDCl$_3$) δ 6.57 (s, 2H), 6.52 (s, 1H), 2.51 (t, J=7.8 Hz, 2H), 2.18 (t, J=7.8 Hz, 2H), 1.87 (s, 6H); $^{13}$C NMR (150 MHz, CDCl$_3$) δ 186.0, 177.7, 144.6, 135.2, 57.7, 32.6, 29.8, 16.0; IR (cm$^{-1}$) 3194, 2946, 1634, 1341, 902, 761; HRMS (EI) m/z calcd. for C$_{11}$H$_{13}$NO$_2$ [M]$^+$: 191.0946. found: 191.0948.

[Example 25] Preparation of 3-(1,3-dioxoisoindolin-2-yl)-1-azaspiro[4.5]deca-6,9-diene-2,8-dione (23)

3-(1,3-Dioxoisoindolin-2-yl)-1-azaspiro[4.5]deca-6,9-diene-2,8-dione (23) was prepared in the same manner as in Example 20, except that 2-{2-(4-hydroxyphenyl)-1-(5-oxo-1,4,2-dioxazol-3-yl)ethyl}isoindoline-1,3-dione (0.1 mmol) was used as a starting material instead of 3-(4-hydroxyphenethyl)-1,4,2-dioxazol-5-one.

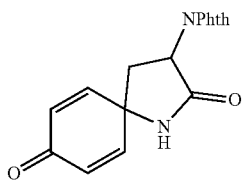

White solid (28 mg, 91%); m.p. 260-262° C.; $^1$H NMR (600 MHz, CDCl$_3$) δ 7.87 (dd, J=5.0, 2.7 Hz, 2H), 7.77 (dd, J=5.0, 2.7 Hz, 2H), 7.19-7.06 (m, 1H), 7.06-6.88 (m, 1H), 6.58 (s, 1H), 6.37-6.20 (m, 2H), 5.17 (t, J=9.9 Hz, 1H), 2.79-2.69 (m, 1H), 2.64-2.49 (m, 1H); $^{13}$C NMR (150 MHz, CDCl$_3$) δ 184.2, 171.5, 167.4, 149.3, 148.4, 134.7, 131.8, 129.7, 128.8, 123.9, 54.7, 48.3, 35.8; IR (cm$^{-1}$) 3353, 1703, 1391, 1117, 860, 714; HRMS (EI) m/z calcd. for C$_{17}$H$_{12}$N$_2$O$_4$ [M]$^+$: 308.0797. found: 308.0801.

[Example 26] Preparation of 8-methoxy-1-azaspiro[4.5]deca-7,9-diene-2,6-dione (24)

8-Methoxy-1-azaspiro[4.5]deca-7,9-diene-2,6-dione (24) was prepared in the same manner as in Example 20, except that 3-(2-hydroxy-4-methoxyphenethyl)-1,4,2-dioxazol-5-one (0.1 mmol) was used as a starting material instead of 3-(4-hydroxyphenethyl)-1,4,2-dioxazol-5-one.

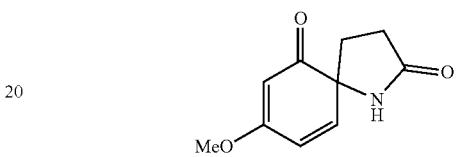

White solid (19 mg, 99%): m.p. 127-129° C.; $^1$H NMR (600 MHz, CDCl$_3$) δ 6.38 (d, J=10.0 Hz, 1H), 6.19-6.07 (m, 2H), 5.41 (d, J=2.3 Hz, 1H), 3.79 (s, 3H), 2.75-2.58 (m, 1H), 2.45-2.20 (m, 2H), 2.08-1.95 (m, 1H); $^{13}$C NMR (150 MHz, CDCl$_3$) δ 199.7, 179.6, 170.7, 143.5, 123.1, 97.8, 64.3, 56.3, 32.4, 28.5; IR (cm$^{-1}$) 3210, 1673, 1572, 1412, 1206, 995, 633; HRMS (EI) m/z calcd. for C$_{10}$H$_{11}$NO$_3$ [M]$^+$: 193.0739. found: 193.0741.

[Example 27] Preparation of 2H-Spiro[naphthalene-1,2'-pyrrolidine]-2,5'-dione (25)

2H-Spiro[naphthalene-1,2'-pyrrolidine]-2,5'-dione (25) was prepared in the same manner as in Example 20, except that 3-{2-(2-hydroxynaphthalen-1-yl)ethyl}-1,4,2-dioxazol-5-one (0.1 mmol) was used as a starting material instead of 3-(4-hydroxyphenethyl)-1,4,2-dioxazol-5-one.

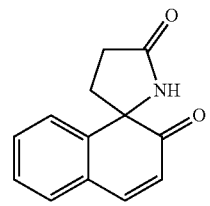 [SMILES: O=C1CCC2(N1)C(=O)C=Cc1ccccc12]

White solid (21 mg, 99%); m.p. 216-218° C.; 1H NMR (600 MHz, CDCl$_3$) δ 7.61 (d, J=7.7 Hz, 1H), 7.49-7.43 (m, 2H), 7.40-7.33 (m, 2H), 6.20 (d, J=9.9 Hz, 1H), 5.95 (s, 1H), 2.59-2.49 (m, 2H), 2.49-2.39 (m, 1H), 2.09-1.98 (m, 1H); $^{13}$C NMR (150 MHz, CDCl$_3$) δ 200.4, 179.3, 145.4, 143.4, 131.1, 130.1, 129.7, 128.8, 125.6, 123.5, 68.8, 36.7, 28.3; IR (cm$^{-1}$) 3167, 3070, 2922, 1672, 1353, 1086, 751; HRMS (EI) m/z calcd. for C$_{13}$H$_{11}$NO$_2$ [M]$^+$: 213.0790, found: 213.0792.

[Example 28] Preparation of 1-azaspiro[3.5]nona-5,8-diene-2,7-dione (26)

1-Azaspiro[3.5]nona-5,8-diene-2,7-dione (26) was prepared in the same manner as in Example 20, except that 3-(4-hydroxybenzyl)-1,4,2-dioxazol-5-one (0.1 mmol) was used as a starting material instead of 3-(4-hydroxyphenethyl)-1,4,2-dioxazol-5-one.

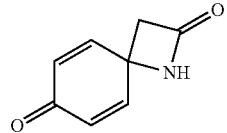 [SMILES: O=C1C=CC2(C=C1)CC(=O)N2]

White solid (9 mg, 63%); m.p. 158-160° C.; 1H NMR (600 MHz, CDCl$_3$) δ 6.96 (d, J=9.8 Hz, 2H), 6.58-6.12 (m, 3H), 3.26 (s, 2H); $^{13}$C NMR (150 MHz, CDCl$_3$) δ 184.6, 164.9, 148.2, 130.8, 51.0, 50.1; IR (cm$^{-1}$) 3292, 1748, 1661, 1617, 1396, 1260, 866; HRMS (EI) m/z calcd. for C$_8$H$_7$NO$_2$ [M]$^+$: 149.0477. found: 149.0475.

[Example 29] Preparation of Di-Spiroindoline Compound A (27)

Di-spiroindoline compound A (27) was prepared in the same manner as in Example 20, except that 3-{2-(4-methoxy-1H-indol-3-yl) ethyl}-1,4,2-dioxazol-5-one (0.1 mmol) was used as a starting material instead of 3-(4-hydroxyphenethyl)-1,4,2-dioxazol-5-one.

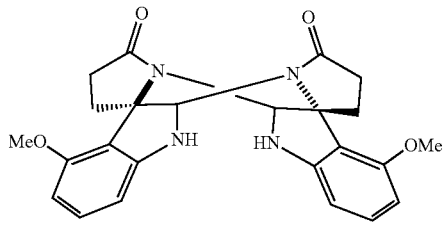 [SMILES: COc1cccc2c1[C@]1(CCC(=O)N1C)C(N1C(=O)CC[C@]13c1c(cccc1OC)NC3C)N2]

Yellow solid (12 mg, 56%); m.p. 286-288° C.; 1H NMR (600 MHz, CDCl$_3$) δ 6.67 (t, J=8.0 Hz, 2H), 6.07 (d, J=8.2 Hz, 2H), 5.64 (d, J=7.8 Hz, 2H), 5.59 (s, 2H), 3.80 (s, 6H), 2.79-2.67 (m, 2H), 2.53-2.43 (m, 2H), 2.43-2.36 (m, 2H), 2.32-2.22 (m, 2H); $^{13}$C NMR (150 MHz, CDCl$_3$) δ 176.2, 156.0, 150.0, 131.4, 115.0, 103.1, 101.4, 72.8, 65.8, 55.3, 34.2, 30.3; IR (cm$^{-1}$) 3272, 2939, 1676, 1608, 1365, 1252, 1083, 728; HRMS (EI) m/z calcd. for C$_{24}$H$_{24}$N$_4$O$_4$ [M]$^+$: 432.1798. found: 432.1801.

[Example 30] Preparation of Di-Spiroindoline Compound B (28)

Di-spiroindoline compound B (28) was prepared in the same manner as in Example 20, except that 3 3-{2-(1-methyl-1H-indol-3-yl)ethyl}-1,4,2-dioxazol-5-one (0.1 mmol) was used as a starting material instead of 3-(4-hydroxyphenethyl)-1,4,2-dioxazol-5-one.

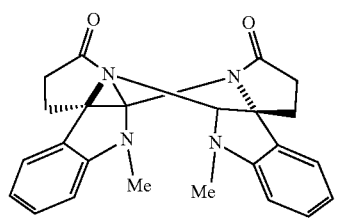

Yellow solid (15 mg, 77%); m.p. 204-206° C.; 1H NMR (600 MHz, CDCl$_3$) δ 7.02 (d, J=7.3 Hz, 2H), 6.94 (t, J=7.6 Hz, 2H), 6.55 (t, J=7.4 Hz, 2H), 5.84 (d, J=7.8 Hz, 2H), 5.57 (s, 2H), 2.88-2.77 (m, 2H), 2.61-2.51 (m, 2H), 2.50-2.41 (m, 2H), 2.36-2.24 (m, 8H); $^{13}$C NMR (150 MHz, CDCl$_3$) δ 176.1, 149.0, 130.0, 129.3, 122.1, 116.8, 105.1, 75.6, 65.4, 34.9, 30.2, 30.0; IR (cm$^{-1}$) 3053, 2927, 1686, 1607, 1343, 1226, 729; HRMS (EI) m/z calcd. for C$_{24}$H$_{24}$N$_4$O$_2$ [M]$^+$: 400.1899. found: 400.1899.

Comparative Example 3

5-Methoxyindolin-2-one was prepared in the same manner as in Example 3, except that Catalyst C was used instead of Catalyst A.

As a result, 5-methoxyindolin-2-one and 7-methoxyindolin-2-one were prepared at 5% or less, respectively.

Comparative Example 4

5-Methoxyindolin-2-one was prepared in the same manner as in Example 3, except that Catalyst D was used instead of Catalyst A.

As a result, 5-methoxyindolin-2-one was not prepared at all.

The method of preparing a lactam compound according to the Examples of the present invention may produce a lactam compound by using a specific solvent, but in Comparative Examples 3 and 4 using Catalyst C and Catalyst D having different ligands from the catalyst of the present invention, a lactam compound was not prepared.

Therefore, the method of preparing a lactam compound of the present invention using a specific catalyst and a specific starting material may be very useful for preparation of a lactam compound.

The invention claimed is:
1. A method of preparing a lactam compound, the method comprising: amidating a 3-substituted dioxazol-one compound in the presence of a catalyst represented by the following Chemical Formula 1 and a base to prepare a lactam compound:

[Chemical Formula 1]

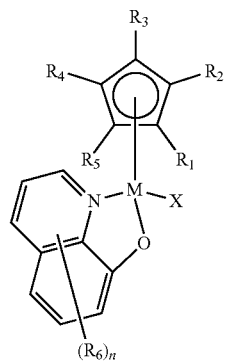

wherein
M is iridium, rhodium, ruthenium, or cobalt;
X is a halogen;
R1 to R5 are independently of one another hydrogen or (C1-C7)alkyl; and
R6 is a halogen, (C1-C20)alkyl, halo(C1-C20)alkyl, (C1-C20)alkoxy, (C6-C20)aryl, or (C3-C20)heteroaryl; and
n is an integer of 0 to 6.

2. The method of preparing a lactam compound of claim 1, wherein amidating a 3-substituted dioxazol-one compound of the following Chemical Formula 2 in the presence of the catalyst represented by Chemical Formula 1 and the base to prepare a lactam compound of the following Chemical Formula 3 is included:

[Chemical Formula 2]

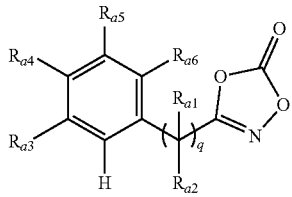

[Chemical Formula 3]

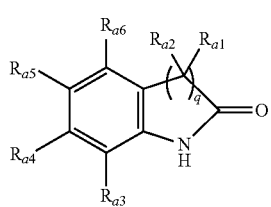

wherein

Ra1 and Ra2 are independently of each other hydrogen, (C1-C20)alkyl, (C6-C20)aryl, or (C3-C20)heterocycalkyl;

Ra3 to Ra6 are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

3. The method of preparing a lactam compound of claim 1, wherein amidating a 3-substituted dioxazol-one compound of the following Chemical Formula 4 in the presence of the catalyst represented by Chemical Formula 1 and the base to prepare a lactam compound of the following Chemical Formula 5 is included:

[Chemical Formula 4]

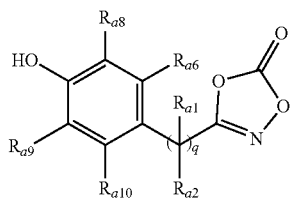

[Chemical Formula 5]

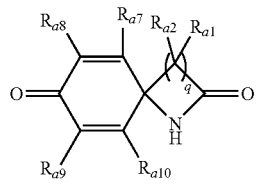

wherein

Ra1 and Ra2 are independently of each other hydrogen, (C1-C20)alkyl, (C6-C20)aryl, or (C3-C20)heterocycalkyl;

Ra7 to Ra10) are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring;

q is an integer of 1 or 2.

4. The method of preparing a lactam compound of claim 1, wherein amidating a 3-substituted dioxazol-one compound of the following Chemical Formula 6 in the presence of the catalyst represented by Chemical Formula 1 and the base to prepare a lactam compound of the following Chemical Formula 7 is included:

[Chemical Formula 6]

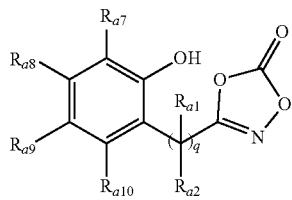

[Chemical Formula 7]

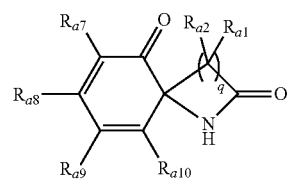

wherein

Ra1 and Ra2 are independently of each other hydrogen, (C1-C20)alkyl, (C6-C20)aryl, or (C3-C20)heterocycloalkyl;

Ra7 to Ra11) are independently of one another hydrogen, a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl, or may be connected to an adjacent substituent to form an aromatic ring or an alicyclic ring with or without a fused ring; and q is an integer of 1 or 2.

5. The method of preparing a lactam compound of claim 1, wherein amidating a 3-substituted dioxazol-one compound of the following Chemical Formula 8 in the presence of the catalyst represented by Chemical Formula 1 and the base to prepare a lactam compound of the following Chemical Formula 9 is included:

[Chemical Formula 8]

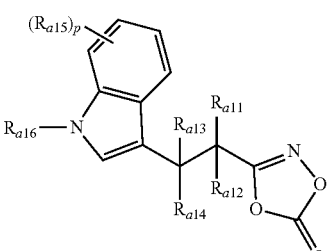

-continued

[Chemical Formula 9]

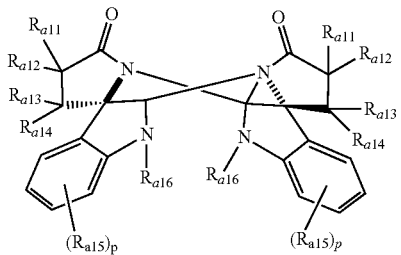

wherein

Ra11 to Ra14 are independently of one another hydrogen or (C1-C20)alkyl;

Ra15 is a halogen, (C1-C20)alkyl, halo(C1-C20)alkyl, (C2-C20)alkenyl, (C2-C20)alkynyl, (C1-C20)alkoxy, (C6-C20)aryl, or (C3-C20)heteroaryl;

Ra16 is hydrogen or (C1-C20)alkyl; and p is an integer of 0 to 4.

6. The method of preparing a lactam compound of claim 1, wherein the catalyst is used at 0.01 to 0.1 mol with respect to 1 mol of the 3-substituted dioxazol-one compound.

7. The method of preparing a lactam compound of claim 1, wherein the base is one or two or more selected from NaBArF4, AgSbF6, AgNTf2, AgBF4, AgPF6, AgOTf, and AgOAc.

8. The method of preparing a lactam compound of claim 1, wherein the base is used at 0.01 to 0.1 mol with respect to 1 mol of the 3-substituted dioxazol-one compound.

9. The method of preparing a lactam compound of claim 1, wherein the amidating is performed at 20 to 80° C.

10. The method of preparing a lactam compound of claim 1, wherein in Chemical Formula 1, M is iridium, X is chloro, R1 to R5 are independently of one another (C1-C30)alkyl, R6 is a halogen, and n is an integer of 0 to 2.

11. The method of preparing a lactam compound of claim 2, wherein

Ra1 and Ra2 are independently of each other hydrogen, (C6-C20)aryl, or phthalimido;

Ra3 to Ra6 are independently of one another hydrogen, a halogen, (C1-C20)alkyl, halo(C1-C20)alkyl, or (C1-C20)alkoxy, or may be connected to an adjacent substituent to form an aromatic ring with or without a fused ring; and q is an integer of 1 or 2.

12. The method of preparing a lactam compound of claim 3, wherein

Ra1 and Ra2 are independently of each other hydrogen or phthalimido;

Ra7 to Ra10 are independently of one another hydrogen, a halogen, (C1-C20)alkyl, or (C1-C20)alkoxy, or may be connected to an adjacent substituent to form an aromatic ring with or without a fused ring; and q is an integer of 1 or 2.

13. The method of preparing a lactam compound of claim 5, wherein

Ra11 to Ra14 are independently of one another hydrogen;

Ra15 is a halogen, (C1-C20)alkyl, or (C1-C20)alkoxy;

Ra16 is hydrogen or (C1-C20)alkyl; and q is an integer of 0 or 1.

14. The method of preparing a lactam compound of claim 4, wherein

Ra1 and Ra2 are independently of each other hydrogen or phthalimido;

Ra7 to Ra10) are independently of one another hydrogen, a halogen, (C1-C20)alkyl, or (C1-C20)alkoxy, or may be connected to an adjacent substituent to form an aromatic ring with or without a fused ring; and q is an integer of 1 or 2.

* * * * *